United States Patent
Storey et al.

(10) Patent No.: US 8,231,858 B2
(45) Date of Patent: Jul. 31, 2012

(54) DIAGNOSTIC IMAGING AGENTS WITH MMP INHIBITORY ACTIVITY

(75) Inventors: Anthony Storey, Amersham (GB); Julie Davis, Amersham (GB); Sally-Ann Ricketts, Amersham (GB); Marivi Mendizabal, Amersham (GB); Alan Cuthbertson, Oslo (NO); Joseph Arukwe, Oslo (NO); Kirsty Heywood, Amersham (GB); Ian Wilson, Amersham (GB); Duncan Wynn, Amersham (GB); Michael Schafers, Munster (DE); Bodo Levkau, Munster (DE); Stefan Wagner, Munster (DE); Hans-Jörg Breyholz, Munster (DE); Klaus Kopka, Munster (DE)

(73) Assignee: GE Healthcare Limited, Little Chalfont (GB)

( * ) Notice: Subject to any disclaimer, the term of this patent is extended or adjusted under 35 U.S.C. 154(b) by 1101 days.

(21) Appl. No.: 10/544,945

(22) PCT Filed: Feb. 10, 2004

(86) PCT No.: PCT/GB2004/000524
§ 371 (c)(1),
(2), (4) Date: May 18, 2006

(87) PCT Pub. No.: WO2004/069365
PCT Pub. Date: Aug. 19, 2004

(65) Prior Publication Data
US 2007/0071670 A1    Mar. 29, 2007

(30) Foreign Application Priority Data

Feb. 10, 2003 (GB) .................................. 0302891.7
Apr. 1, 2003 (GB) .................................. 0307524.9

(51) Int. Cl.
*A61K 51/00* (2006.01)
*A61M 36/14* (2006.01)

(52) U.S. Cl. ..................................... 424/1.11; 424/1.85

(58) Field of Classification Search ........................ None
See application file for complete search history.

(56) References Cited

U.S. PATENT DOCUMENTS
4,427,646 A * 1/1984 Olexa et al. .................. 424/1.69

FOREIGN PATENT DOCUMENTS

| WO | 96/00214 | 1/1996 |
|---|---|---|
| WO | 97/22587 | 6/1997 |
| WO | WO 9850348 A1 * | 11/1998 |
| WO | 01/60416 | 8/2001 |
| WO | 01/60820 | 8/2001 |
| WO | 01/92244 | 12/2001 |

OTHER PUBLICATIONS

Keston et al. (J. Am. Chem. Soc. 1949, 71, 249-257).*
Zheng Q-H, et.al. "Synthesis and Preliminary biological Evaluation of MMP Inhibitor Radiotracers [$^{11}$C]methyl-halo-CGS 27023A Analogs, New Potential PET Breast Cancer Imaging Agents" Nuclear Medicine and Biology, Elsevier Science Publishers, NY vol. 29, No. 7, Oct. 2002 pp. 761-770.
MacPherson, L.J., et.al. "Discovery of CGS 27023A, a non-peptidic, Potent and Orally Active Stromelysin Inhibitor that Blocks Cartilage Degradation in Rabbits" Journal of Medicinal Chemistry, American Chemical society. Washington, vol. 40, No. 16, 1997, pp. 2525-2532.
Rajopadhye M., et.al. "Synthesis and Technetum-99M labeling of Cyclic GP IIB/IIIA Receptor Antagonists Conjugated to 4,5-bis(mercaptoacetamido)-pentanoic acid (MAPT)" Bioorganic & Medicinal Chemistry Letters, Oxford, GB, vol. 6, No. 15, Aug. 6, 1996 pp. 1737-1740.
GB Search Report 0307524.9 dated Aug. 14, 2003.
GB Search Report 0302891.7 dated Jul. 11, 2003.
Int'l Search Report PCT/GB2004/000524 dated Jun. 18, 2004.
Int'l Search Report PCT/GB2004/000524 dated Jun. 25, 2004.
Int'l Preliminary Exam Report PCT/GB2004/000524.

* cited by examiner

*Primary Examiner* — Michael G Hartley
*Assistant Examiner* — Melissa Perreira

(57) ABSTRACT

The present invention relates to the field of diagnostic imaging. Specifically, the invention relates to the diagnostic imaging of diseases where specific matrix metalloproteinases are known to be involved. One embodiment of the invention is a compound having matrix metalloproteinase inhibitory activity suitable for diagnostic imaging. Also disclosed in the present invention is a pharmaceutical composition comprising the diagnostic imaging agent of the invention in a form suitable for mammalian administration. The invention furthermore discloses intermediates in the synthesis of the diagnostic imaging agents of the invention and kits for the preparation of the pharmaceutical composition of the invention. The pharmaceutical composition of the invention may be used in the diagnosis of diseases where specific matrix metalloproteinases are known to be involved.

8 Claims, 12 Drawing Sheets

Formula V

X = OMe
OBn
Br
I

Formula VI

X = OMe (CGS 27023)
OH (Compound 13)
Br (Compound 14)
I (Compound 9)

when X = OBn

H₂, Pd/C,
MeOH

HCl (gas)
dichloroethane

Synthetic Route A

Synthetic Route B

DIAGNOSTIC IMAGING AGENTS WITH MMP INHIBITORY ACTIVITY

This application is a filing under 35 U.S.C. 371 of international application number PCT/GB2004/000524, filed Feb. 10, 2004, which claims priority to application number 0302891.7 filed Feb. 10, 2003 and 0307524.9 filed Apr. 1, 2003, in Great Britain the entire disclosure of which is hereby incorporated by reference.

TECHNICAL FIELD OF THE INVENTION

The present invention relates to the field of in vivo diagnostic Imaging and In particular to SPECT imaging. The present invention specifically relates to novel imaging agents comprising matrix metalloproteinase inhibitors, said novel imaging agents being useful in in vivo diagnostic imaging of cardiovascular disease, inflammatory disease and malignant diseases.

DESCRIPTION OF RELATED ART

The matrixmetalloproteinases (MMPs) are a family of at least 20 zinc-dependent endopeptidases which mediate degradation, or remodelling of the extracellular matrix (ECM) [Massova et al FASEB J (1998) 12 1075-95]. Together, the members of the MMP family can degrade all of the components of the blood vessel wall and therefore play a major role in both physiological and pathological events that involve the degradation of components of the ECM. Since the MMPs can interfere with the call-matrix interactions that control cell behaviour, their activity affects processes as diverse as cellular differentiation, migration, proliferation and apoptosis [Nagase and Woessner J. Biol. Chem. (1999) 274 21491-4]. The negative regulatory controls that finely regulate MMP activity In physiological situations do not always function as they should. Inappropriate expression of MMP activity is thought to constitute part of the pathological mechanism in several disease states. MMPs are therefore targets for therapeutic inhibitors in many inflammatory, malignant and degenerative diseases [Whittaker et al Chem. Rev. (1999) 99 2735-76].

Consequently, it is believed that synthetic inhibitors of MMPs may be useful In the treatment of many inflammatory, malignant and degenerative diseases. Furthermore, it has been suggested that inhibitors of MMPs may be useful in the diagnosis of these diseases. WO 01/60416 discloses compounds which are proposed to be useful in the diagnosis of cardiovascular pathologies associated with extracellular matrix degradation such as atherosclerosis, heart failure and restenosis. The compounds disclosed therein comprise MMP inhibitors linked, via an optional linker, to a chelator capable of conjugating to a diagnostic metal. Preferred MMP inhibitors, chelators and linkers are described therein. A report by Zheng et al [Nuc. Med. Biol. 29 761-770 (2002)] documented the synthesis of MMP inhibitors labelled with the positron emission tomography (PET) tracers $^{11}$C and $^{18}$F. The compounds described therein are postulated to be useful in the non-invasive imaging of breast cancer.

SUMMARY OF THE INVENTION

Novel diagnostic imaging agents having MMP inhibitory activity are disclosed which have been found to be particularly useful in diagnostic imaging. Another aspect of the present invention is a pharmaceutical composition useful in diagnostic imaging of the human body. Kits for the preparation of the pharmaceutical composition of the invention are also disclosed. Furthermore, the invention encompasses the use of the pharmaceutical composition of the invention for diagnostic imaging.

The imaging agents of the present invention are useful for the in vivo diagnostic imaging of a range of disease states (inflammatory, malignant and degenerative diseases) where specific matrix metalloproteinases are known to be involved. These include:

(a) atherosclerosis, where various MMPs are overexpressed. Elevated levels of MMP-1, 3, 7, 9, 11, 12, 13 and MT1-MMP have been detected in human atherosclerotic plaques [S. J. George, Exp. Opin. Invest. Drugs, 9(5), 993-1007 (2000) and references therein]. Expression of MMP-2 [Z. Li et al, Am. J. Pathol., 148, 121-128 (1996)] and MMP-8 [M. P. Herman et al, Circulation, 104, 1899-1904 (2001)] in human atheroma has also been reported;

(b) CHF (Peterson, J. T. et al. Matrix metalloproteinase inhibitor development for the treatment of heart failure, Drug Dev. Res. (2002), 55(1), 29-44 reports that MMP-1, MMP-2, MMP-3, MMP-8, MMP-9, MMP-13 and MMP-14 are upregulated in heart failure);

(c) cancer [Vihinen et al, Int. J. Cancer 99, p157-166 (2002) reviews MMP involvement in cancers, and particularly highlights MMP-2, MMP-3, MMP-7, and MMP-9];

(d) arthritis [Jacson et al, Inflamm. Res. 50(4), p183-186 (2001) "Selective matrix metalloproteinase inhibition in rheumatoid arthritis—targeting gelatinase A activation", MMP-2 is particularly discussed];

(e) amyotrophic lateral sclerosis [Lim et al, J. Neurochem, 67, 251-259 (1996); where MMP-2 and MMP-9 are involved];

(f) brain metastases, where MMP-2, MMP-9 and MMP-13 have been reported to be implicated [Spinale, Circul. Res., 90, 520-530 (2002)];

(g) cerebrovascular diseases, where MMP-2 and MMP-9 have been reported to be involved [Lukes et al, Mol. Neurobiol., 19, 267-284 (1999)];

(h) Alzheimer's disease, where MMP-2 and MMP-9 have been identified in diseased tissue [Backstrom et al, J. Neurochem., 58, 983-992 (1992)];

(i) neuroinflammatory disease, where MMP-2, MMP-3 and MMP-9 are involved [Mun-Bryce et al, Brain. Res., 933, 42-49 (2002)];

(j) COPD (i.e. chronic obstructive pulmonary disease) where MMP-1, MMP-2, MMP-8 and MMP-9 have been reported to be upregulated [Segura-Valdez et al, Chest; 117, 684-694 (2000)];

(k) eye pathology [Kurpakus-Wheater et al, Prog. Histo. Cytochem., 36(3), 179-259 (2001)];

(l) skin diseases [Herouy, Y., Int. J. Mol. Med., 7(1), 3-12 (2001)].

DETAILED DESCRIPTION OF THE INVENTION

A first aspect of the present invention is a diagnostic imaging agent which comprises a matrix metalloproteinase inhibitor of Formula I labelled with a γ-emitting radionuclide:

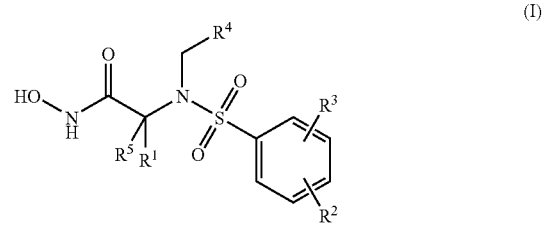

(I)

wherein:
R$^1$ is selected from hydrogen, hydroxy, C$_{1-6}$ alkyl, C$_{6-14}$ aryl, C$_{7-20}$ arylalkyl, or together with R$^5$ and the carbon to which it is attached forms either a C$_{6-8}$ cycloalkyl ring or a C$_{4-6}$ heterocyclic ring, or together with R$^4$ forms a C$_{4-6}$ heterocyclic ring containing 5-7 atoms and 1 or 2 heteroatoms chosen from N or O;
R$^2$ and R$^3$ are independently hydrogen, hydroxy, halogen, C$_{1-6}$ alkyl, C$_{1-6}$ alkoxy, C$_{1-6}$ amino, C$_{6-14}$ aryl, C$_{7-20}$ arylalkyl or C$_{7-20}$ carbamoylaryl;
R$^4$ is C$_{6-14}$ aryl, C$_{4-6}$ heteroaryl, C$_{7-20}$ arylalkyl, C$_{7-20}$ carbamoylaryl or arylcarbamoylaryl; and,
R$^5$ is selected from hydrogen or C$_{1-6}$ alkyl,
such that when R$^1$ is isopropyl, R$^3$ is hydrogen and R$^4$ is 3-pyridyl, then R$^2$ is not methoxy.

"Alkyl" used either alone or as part of another group (e.g. hydroxyalkyl, aminoalkyl, carboxyalkyl or alkyoxyalkyl) is defined herein as any straight, branched or cyclic, saturated or unsaturated C$_x$H$_{2x+1}$ group, wherein unless otherwise specified x is an integer between 1 and 6.

"Aryl" used either alone or as part of another group is defined herein as any C$_{6-14}$ molecular fragment or group which is derived from a monocyclic or polycyclic aromatic hydrocarbon. Suitable aryl groups of the invention are phenyl or naphthyl groups which are optionally substituted at any position.

An "arylalkyl" is defined in the present invention as any C$_{7-20}$ group consisting of an alkyl group and an aryl group as defined above.

"Heterocyclic ring" is defined in the present invention as a C$_{4-6}$ cyclic group comprising 1 or 2 heteroatoms. Suitable heteroatoms include N and O.

The term "halogen" means a group selected from fluorine, chlorine, bromine, and iodine.

An "amine" is defined in the present invention as any organic group that contains an amino or a substituted amino group.

The phrase "labelled with a γ-emitting radionuclide" used herein means that one of the atoms or substituents of Formula I comprises a γ-emitting radionuclide either as an artificially enriched level of an atom intrinsic to the substructure, or as an additional essential feature that has been chemically attached via a functionality suitable for coupling said γ-emitting radionuclide.

A preferred diagnostic imaging agent of the invention comprises a compound of Formula I labelled with a γ-emitting radionuclide wherein:
R$^1$ is selected from C$_{1-6}$ alkyl, C$_{6-14}$ aryl, or C$_{7-20}$ arylalkyl, or together with R$^5$ forms a C$_{4-6}$ heterocyclic ring together with the carbon to which it is attached;
R$^2$ is hydrogen, hydroxy, methyl, isopropyl, methoxy or halogen;
R$^3$ is hydrogen;
R$^4$ is pyridyl or (Ar$^1$)$_y$—(R''')(NH)-phenyl wherein Ar$^1$ is phenylene, R''' is CH$_2$ or C=O, y=0 or 1 and z=0 or 1; and,
R$^5$ is hydrogen,
such that when R$^1$ is isopropyl and R$^4$ is 3-pyridyl, then R$^2$ is not methoxy.

A most preferred diagnostic imaging agent of the invention comprises a compound of Formula I labelled with a γ-emitting radionuclide wherein:
R$^1$ is methyl, isobutyl, isopropyl, benzyl or hydroxybenzyl;
R$^2$ is hydroxy, halogen or methoxy;
R$^3$ is hydrogen;
R$^4$ is pyridyl or (Ar$^1$)$_y$—(R''')$_z$(NH)-phenyl wherein Ar$^1$ is 1,4-phenylene, R''' is CH$_2$ or C=O, y=0 or 1 and z=0 or 1; and
R$^5$ is hydrogen,
such that when R$^1$ is isopropyl and R$^4$ is 3-pyridyl, then R$^2$ is not methoxy.

When R$^5$ is hydrogen, the matrix metalloproteinase inhibitor of the present invention includes a chiral centre at the carbon atom bearing the R$^1$ group. Enantiomers at this chiral centre are within the scope of the invention and a preferred such enantiomer is of Formula Ia:

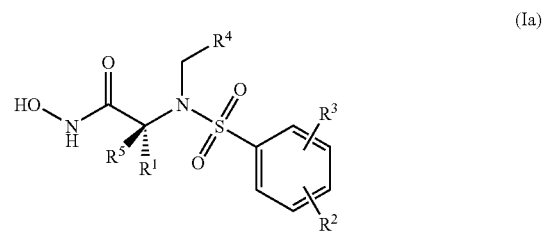

(Ia)

An especially preferred diagnostic imaging agent of the invention comprises a compound of Formula I wherein said γ-emitting radionuclide replaces, or is chemically attached to, one or more of the R$^1$ to R$^4$ substituents. A most especially preferred diagnostic imaging agent of the invention comprises a compound of Formula I wherein R$^2$ is positioned para to the sulfonamide and R$^3$ is positioned meta to the sulfonamide.

Compounds of Formula I not labelled with a γ-emitter can be readily synthesised according to the methods described in MacPherson et al J. Med. Chem. 1997; 2525-32.

Suitable γ-emitting radionuclides of the invention are γ-emitting metal ions or γ-emitting radioactive halogens. These are described in more detail below, including preferred and most preferred embodiments.

When the γ-emitting radionuclide of the invention is a metal ion, it is suitably chosen from $^{99m}$Tc, $^{111}$In, $^{113}$In, $^{67}$Cu or $^{67}$Ga. Preferred γ-emitting metal ions are $^{99m}$Tc, $^{67}$Cu, $^{67}$Ga and $^{111}$In, with $^{99m}$Tc being most preferred. The metal ion is suitably present in the diagnostic imaging agent of the invention as a metal complex such that the diagnostic imaging agent is a metal complex conjugate of Formula II:

[{matrix metalloproteinase inhibitor}-(A)$_n$]$_m$-[metal complex]      (II)

where: -(A)$_n$- is a linker group,
n is an integer of value 0 to 50, and
m is 1, 2 or 3.

By the term "metal complex" is meant a co-ordination complex of the metal ion with one or more ligands. It is strongly preferred that the metal complex is "resistant to transchelation", i.e. does not readily undergo ligand exchange with other potentially competing ligands for the metal co-ordination sites. Potentially competing ligands include the compound of Formula I plus other excipients in the preparation in vitro (e.g. radioprotectants or antimicrobial preservatives used in the preparation), or endogenous compounds in vivo (e.g. glutathions, transferrin or plasma proteins). The "linker group" (A)$_n$ is as defined below for Formula IIa.

A second aspect of the present invention is a ligand conjugate which may be radiolabelled to form the metal complex conjugates of Formula II. Preferred ligand conjugates of the invention are of Formula IIa:

[{matrix metalloproteinase inhibitor}-(A)$_n$]$_m$-[ligand]      (IIa)

where: -(A)$_n$- is a linker group wherein each A is independently CR'$_2$, CR'=CR', C≡C, CH$_2$CH$_2$O, CR'$_2$CO$_2$, CO$_2$CR'$_2$, NR'CO, CONR', NR'(C=O)NR', NR'(C=S) NR', SO$_2$NR', NR'SO$_2$, CR'$_2$OCR'$_2$, CR'$_2$SCR'$_2$, CR'$_2$NRCR'$_2$, a C$_{4-8}$ cycloheteroalkylene group, a C$_{4-8}$ cycloalkylene group, a C$_{5-12}$ arylene group, a C$_{3-12}$ heteroarylene group or an amino acid;

R' is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;

n is an integer of value 0 to 50; and m is 1, 2 or 3.

In Formulae II and IIa, m is preferably 1 or 2, and is most preferably 1.

Suitable ligands for use in the present invention which form metal complex conjugates resistant to transchelation include: chelating agents, where 2-6, preferably 2-4, metal donor atoms are arranged such that 5- or 6-membered chelate rings result (by having a non-co-ordinating backbone of either carbon atoms or non-co-ordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as MIBI (i.e. 1-isocyano-2-methoxy-2-methylpropane). Examples of suitable phosphines include Tetrofosmin, and monodentate phosphines such as tris(3-methoxypropyl)phosphine. Examples of suitable diazenides include the HYNIC series of ligands i.e. hydrazine-substituted pyridines or nicotinamides.

Examples of suitable chelating agents for technetium which form metal complexes resistant to transchelation include, but are not limited to:

(i) diaminedioximes of Formula III:

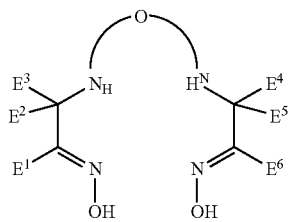

(III)

where E$^1$-E$^6$ are each independently an R" group;

each R" is H or C$_{1-10}$ alkyl, C$_{3-10}$ alkylaryl, C$_{2-10}$ alkoxyalkyl, C$_{1-10}$ hydroxyalkyl, C$_{1-10}$ fluoroalkyl, C$_{2-10}$ carboxyalkyl or C$_{1-10}$ aminoalkyl, or two or more R" groups together with the atoms to which they are attached form a carbocyclic, heterocyclic, saturated or unsaturated ring, and wherein one or more of the R" groups is conjugated to the compound of Formula I;

and Q is a bridging group of formula -(J)$_f$-;

where f is 3, 4 or 5 and each J is independently —O—, —NR"— or —C(R")$_2$— provided that -(J)$_f$- contains a maximum of one J group which is —O— or —NR"—.

Preferred Q groups are as follows:

Q=—(CH$_2$)(CHR")(CH$_2$)— i.e. propyleneamine oxime or PnAO derivatives;

Q=—(CH$_2$)$_2$(CHR")(CH$_2$)$_2$— i.e. pentyleneamine oxime or PentAO derivatives;

Q=—(CH$_2$)$_2$NR"(CH$_2$)$_2$—.

E$^1$ to E$^6$ are preferably chosen from: C$_{1-3}$ alkyl, C$_{4-10}$ alkylaryl C$_{2-3}$ alkoxyalkyl, C$_{1-3}$ hydroxyalkyl, C$_{1-2}$ fluoroalkyl, C$_{1-3}$ carboxyalkyl or C$_{1-3}$ aminoalkyl. Most preferably, each E$^1$ to E$^6$ group is CH$_3$.

The compound of Formula I is preferably conjugated at either the E$^1$ or E$^8$ R" group, or an R" group of the Q moiety. Most preferably, the compound of Formula I is conjugated to an R" group of the Q moiety. When the compound of Formula I is conjugated to an R" group of the Q moiety, the R" group is preferably at the bridgehead position. In that case, Q is preferably —(CH$_2$)(CHR")(CH$_2$)—, —(CH$_2$)$_2$(CHR") (CH$_2$)$_2$— or —(CH$_2$)$_2$NR"(CH$_2$)$_2$—, most preferably —(CH$_2$)$_2$(CHR")(CH$_2$)$_2$—.

An especially preferred bifunctional diaminedioxime chelator has the following structure:

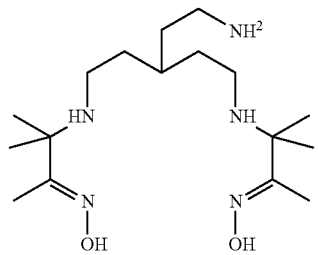

such that the compound of Formula I is conjugated via the bridgehead —CH$_2$CH$_2$NH$_2$ group. This bifunctional diaminedioxime chelator will be referred to in the rest of this document as chelating agent 1, or CA1.

(ii) N$_3$S ligands having a thioltriamide donor set such as MAG$_3$ (mercaptoacetyltriglycine) and related ligands; or having a diamidepyridinethiol donor set such as PICA;

(iii) N$_2$S$_2$ ligands having a diaminedithiol donor set such as BAT or ECD (i.e. ethylcysteinate dimer), or an amideaminedithiol donor set such as MAMA;

(iv) N$_4$ ligands which are open chain or macrocyclic ligands having a tetramine, amidetriamine or diamidediamine donor set, such as cyclam, monoxocyclam or dioxocyclam.

(v) N$_2$O$_2$ ligands having a diaminediphenol donor set.

The above described ligands are particularly suitable for complexing $^{99m}$Tc, and are described more fully by Jurisson et al [Chem. Rev. (1999) 99 2205-2218]. Other suitable ligands are described in Sandoz WO 91/01144, which includes ligands which are particularly suitable for indium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. When the radiometal ion is technetium, the ligand is preferably a chelating agent which is tetradentate. Preferred chelating agents for technetium are the diaminedioximes, or those having an $N_2S_2$ or $N_3S$ donor set as described above. Especially preferred chelating agents for technetium are the diaminedioximes.

It is envisaged that the role of the linker group $-(A)_n-$ of Formula II is to distance the relatively bulky metal complex, from the active site of the compound of Formula I, so that binding of the compound to the MMP enzyme is not impaired. This can be achieved by a combination of flexibility (e.g. simple alkyl chains), so that the bulky group has the freedom to position itself away from the active site and/or rigidity such as a cycloalkyl or aryl spacer which orientates the metal complex away from the active site.

The nature of the linker group can also be used to modify the biodistribution of the resulting metal complex conjugate. Thus, e.g. the introduction of ether groups in the linker will help to minimise plasma protein binding. Linkers comprising a number of linked —$CH_2CH_2O$— groups (PEG linkers) or a peptide chain of 1-10 amino acids have the additional property of allowing favourable modification of the clinical properties of a particular compound, notably the biodistribution. Such "biomodifier" linker groups may accelerate the clearance of the imaging agent from background tissue, such as muscle or liver, and/or from the blood, thus giving a better diagnostic image due to less background interference. A biomodifier linker group may also be used to favour a particular route of excretion, e.g. via the kidneys as opposed to via the liver.

Non-peptide linker groups such as alkylene groups or arylene groups have the advantage that there are no significant hydrogen bonding interactions with the conjugated compound of Formula I, so that the linker does not wrap round onto the compound of Formula I. Preferred alkylene spacer groups are —$(CH_2)_q$— where q is 2 to 5. Preferred arylene spacers are of Formula IV:

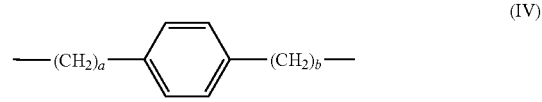

where: a and b are independently 0, 1 or 2.

When the linker group does not comprise PEG or a peptide chain, preferred linker groups $-(A)_n-$ have a backbone chain of linked atoms which make up the $-(A)_n-$ moiety of 2 to 10 atoms, most preferably 2 to 5 atoms, with 2 or 3 atoms being especially preferred. A minimum linker group backbone chain of 2 atoms confers the advantage that the chelator is well-separated from the compound of Formula I so that any interaction is minimised. Where the linker group is a PEG linker, the number of A groups n in $-(A)_n-$ may be up to 50, preferably between 15 and 30. Where the linker comprises a peptide chain it is preferably a peptide chain of 1 to 10 amino acid residues, the amino acid residues are preferably chosen from glycine, lysine, aspartic acid or serine.

It is strongly preferred that the compound of Formula I is bound to the metal complex in such a way that the linkage does not undergo facile metabolism in blood, since that would result in the metal complex being cleaved off before the compound reached the desired in vivo target site. The compound of Formula I is therefore preferably covalently bound to the metal complexes of the present invention via linkages which are not readily metabolised.

Most preferred compounds of the invention labelled with a γ-emitting metal ion are labelled with $^{99m}Tc$ co-ordinated to CA1, with CA1 attached via a suitable chemical functionality, with an optional linker, at one of the $R^1$ to $R^4$ substituents of Formula I. Examples of preferred compounds of the invention labelled with $^{99m}Tc$ are illustrated below (Tc stands for $^{99m}Tc$ in the structures):

Compound 1

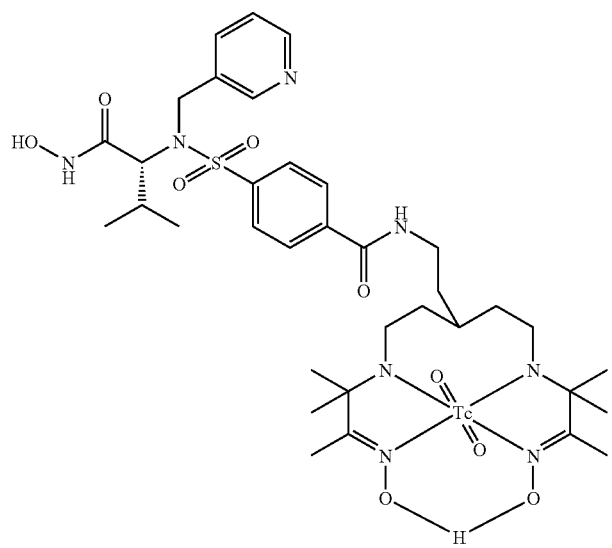

-continued
Compound 2
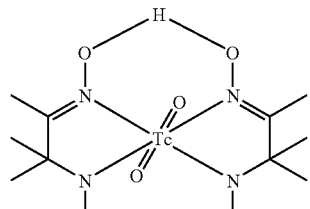
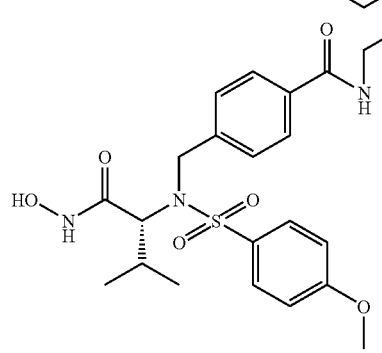
Compound 3
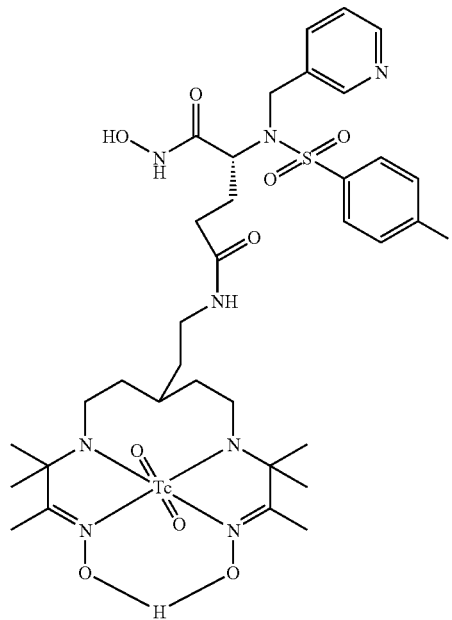
Compound 16
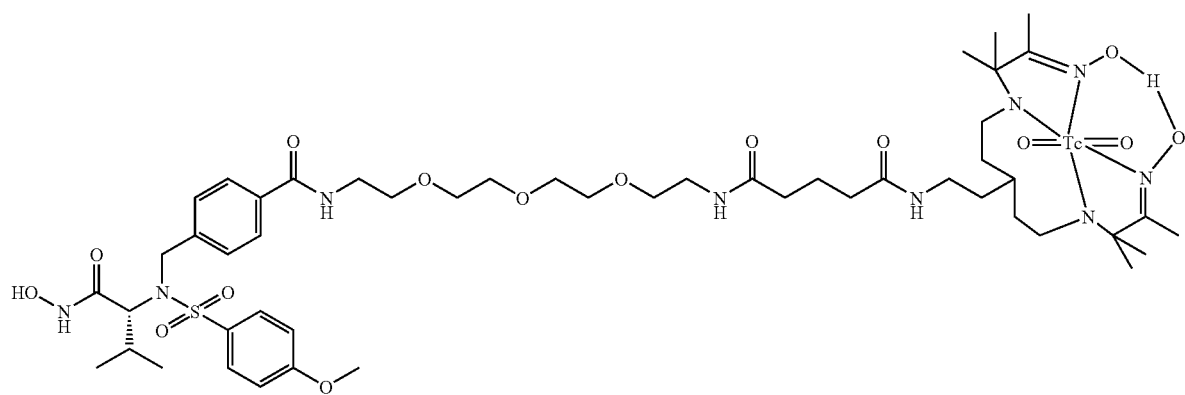

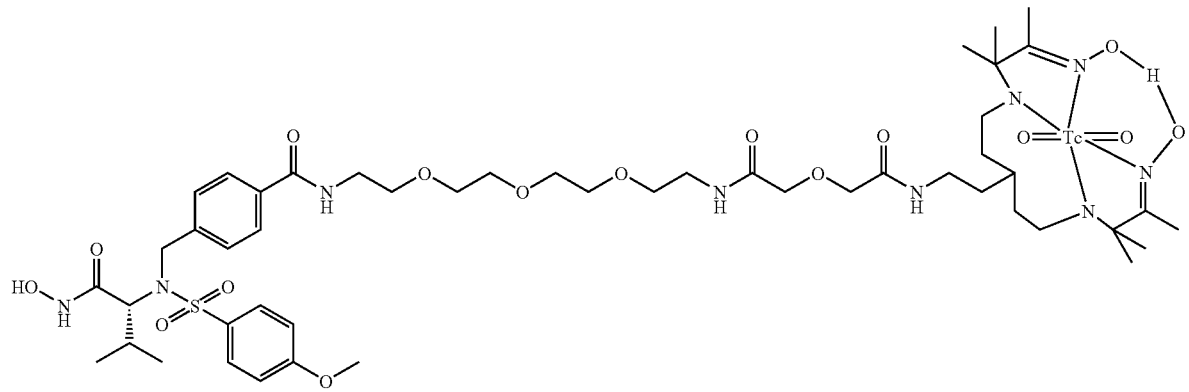

Compound 17

When the γ-emitting radionuclide is a radioactive halogen it is preferably an isotope of iodine and the diagnostic imaging agent is usefully prepared by reacting a precursor with the γ-emitting isotope of iodine. Such precursors are described in more detail below and are a fourth aspect of the present invention. Preferred γ-emitting isotopes of iodine of the present invention are $^{123}$I or $^{131}$I.

The γ-emitting isotope of iodine is preferably attached via a direct covalent bond to an aromatic ring such as a benzene ring, or a vinyl group since it is known that iodine atoms bound to saturated aliphatic systems are prone to in vivo metabolism and hence loss of the γ-emitting isotope of iodine. Most preferably, the γ-emitting isotope of iodine is attached via a direct covalent bond to the —NSO$_2$-phenyl ring of Formula I.

Especially preferred diagnostic imaging agents of the invention labelled with a γ-emitting isotope of iodine are compounds of Formula I wherein:

(i) $R^1$ is isopropyl, $R^2$ is 4-OH, $R^3$ is 3-$^{123}$I and $R^4$ is pyridyl (when $R^4$ is 3-pyridyl=Compound 4);

(ii) $R^1$ is isopropyl, $R^2$ is 4-$^{123}$I, $R^3$ is H and $R^4$ is pyridyl (when $R^4$ is 3-pyridyl=Compound 7);

(iii) $R^1$ is isopropyl, $R^2$ is 4-(4-[$^{123}$I] iodobenzamide), $R^3$ is H and $R^4$ is pyridyl (when $R^4$ is 3-pyridyl=Compound 20);

(iv) $R^1$ is 4-hydroxy-3-[$^{123}$I]iodobenzyl, $R^2$ is 4-iodo, $R^3$ is H and $R^4$ is pyridyl (when $R^4$ is 3-pyridyl=Compound 21); or, (v) $R^1$ is isopropyl, $R^2$ is 4-iodo, $R^3$ is 3-H and $R^4$ is (Ar$^1$)$_y$—(R''')$_z$(NH)—(Ar$^2$) wherein Ar$^1$ is 1,4-phenylene and Ar$^2$ is 4-[$^{123}$I]iodophenyl, R''' can be CH$_2$ or C=O, y=0 or 1 and z=0 or 1;

and wherein when $R^4$ is pyridyl, it is preferably 3-pyridyl.

The non-radioactive analogs of the radioiodinated MMP inhibitors exhibit excellent inhibition against MMP-2, with IC$_{50}$ values of 2.5 nM for Compound 9 (Table 1), and 320 nM for Compound 8 (Table 1). These non-radioactive analogs also display excellent inhibition against MMP-9, with IC$_{50}$ values of 4.6 nM for Compound 9 and 153 nM for Compound 8. Therefore, the compounds of the invention possess in vitro characteristics predictive of successful imaging of MMP activity in vivo. Therefore, using these new radiotracers in combination with SPECT provides an innovative tool for imaging MMP activity non-invasively in vivo. Imaging studies in animal models provide further evidence of the suitability of the agents of the invention for diagnostic imaging of MMP activity in vivo.

In a third aspect, the present invention provides a pharmaceutical composition which comprises the diagnostic imaging agent as described above, together with a biocompatible carrier, in a form suitable for. mammalian administration. The "biocompatible carrier" is a fluid, especially a liquid, which in which the imaging agent can be suspended or dissolved, such that the composition is physiologically tolerable, i.e. it can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like).

A fourth aspect of the present invention is a precursor useful in the preparation of a radioiodinated diagnostic imaging agent of the invention, said precursor comprising a group suitable for reaction with a γ-emitting isotope of iodine to give said diagnostic imaging agent. Suitable precursors of the invention for preparation of radioiodinated imaging agents are compounds of Formula I which comprise a non-radioactive halogen atom such as an aryl iodide or bromide (to permit radioiodine exchange); an activated aryl ring (e.g. a phenol group); an organometallic precursor compound (eg. trialkyltin or trialkylsilyl); or an organic precursor such as triazenes. Methods of introducing a γ-emitting isotope of iodine are described by Bolton [J. Lab. Comp. Radiopharm. 2002 45

485-528]. Examples of suitable aryl groups to which γ-emitting isotopes of iodine can be attached are given below:

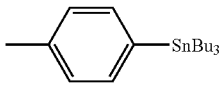 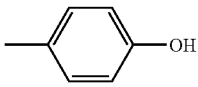

Examples of preferred precursor compounds of the invention in which suitable aryl groups are present are as illustrated below:

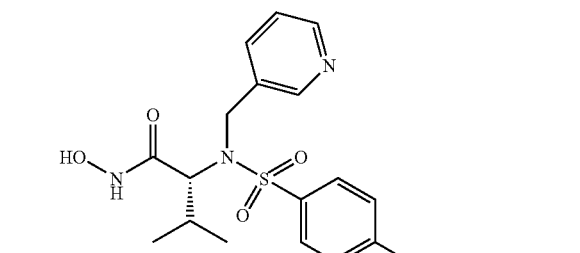

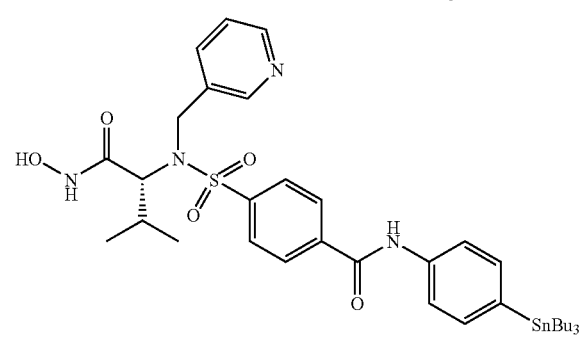

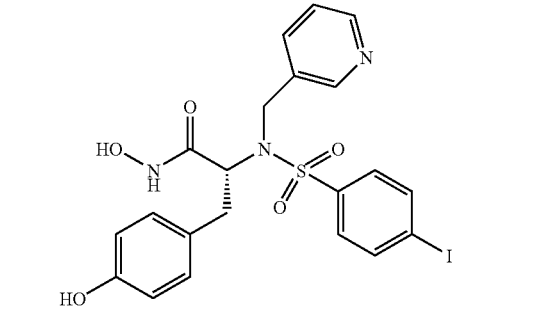

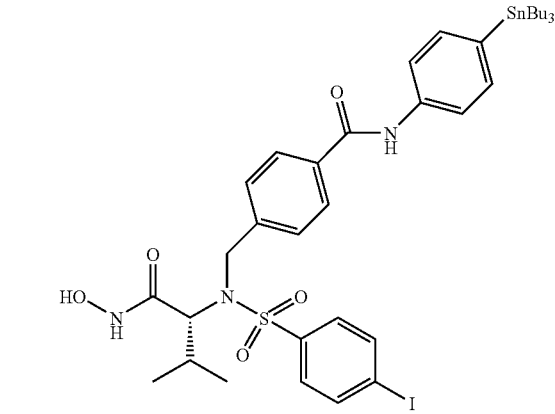

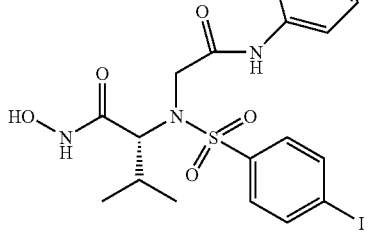

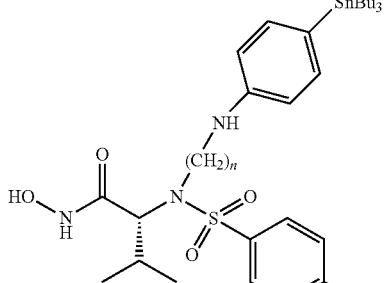

n = 1, 2

Both of the suitable aryl groups discussed above contain substituents which permit facile iodine substitution onto the aromatic ring. Alternative substituents containing γ-emitting isotopes of iodine can be synthesised by direct iodination via radiohalogen exchange, e.g.

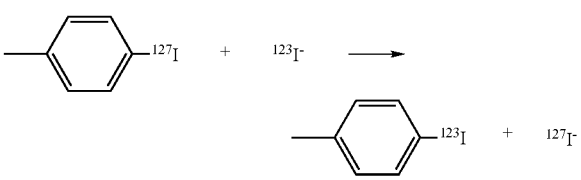

In a fifth aspect, the present invention provides a kit for the preparation of the pharmaceutical composition of the invention. Where the pharmaceutical composition of the invention comprises a diagnostic imaging agent labelled with a γ-emitting radiometal, said kit comprises (i) a ligand conjugate comprising the compound of Formula I conjugated to ligand suitable for the co-ordination of the γ-emitting radiometal, and (ii) a biocompatible reductant. Where the pharmaceutical composition of the invention comprises a diagnostic imaging agent labelled with a γ-emitting isotope of iodine, said kit comprises a precursor which is a compound of Formula I comprising a group suitable for reaction with a γ-emitting isotope of iodine such that reaction of said precursor with a γ-emitting isotope of iodine, typically in the form of iodide, gives said diagnostic imaging agent.

Such kits are designed to give sterile radiopharmaceutical products suitable for human administration, e.g. via direct injection into the bloodstream. For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (e.g. a septum-sealed vial) containing the ligand or chelator conjugate in either free base or acid salt form, together with a biocompatible reductant such as sodium dithionite, sodium bisulphite, ascorbic acid, formamidine sulphinic acid, stannous ion, Fe(II) or Cu(I). The biocompatible reductant is preferably a stannous salt such as stannous chloride or stannous tartrate. Alternatively, the kit may optionally contain a metal complex which, upon addition of the radiometal, undergoes transmetallation (i.e. metal exchange) giving the desired product.

The kits may optionally further comprise additional components such as a transchelator, radioprotectant, antimicrobial preservative, pH-adjusting agent or filler. The "transchelator" is a compound which reacts rapidly to form a weak complex with technetium, then is displaced by the ligand. This minimises the risk of formation of reduced hydrolysed technetium (RHT) due to rapid reduction of pertechnetate competing with technetium complexation. Suitable such transchelators are salts of a weak organic acid, i.e. an organic acid having a pKa in the range 3 to 7, with a biocompatible cation. Suitable such weak organic acids are acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of MDP, i.e. methylenediphosphonic acid, with a biocompatible cation.

By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion, Preferred biocompatible cations are sodium and potassium, most preferably sodium.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (i.e. 2,5-dihydroxybenzoic acid) and salts thereof with a biocompatible cation as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [i.e. tris (hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

A sixth aspect of the present invention is the use of the pharmaceutical composition of the invention for the diagnostic imaging of cardiovascular disease. The pharmaceutical composition of the invention is especially useful for the diagnostic imaging of atherosclerosis and CHF. Use of the diagnostic imaging agents of the invention permits identification of active plaque burden, which allows risk stratification of patients with known or suspected coronary artery disease, i.e. patients with pain or a history of pain, or identified as high risk but asymptomatic. In addition, the diagnostic imaging agents of the invention permit identification of vulnerable plaques in symptomatic patients, which allows identification of high risk of acute myocardial infarction or stroke irrespective of stenosis and permits immediate risk stratification when the patient presents with chest pain. Furthermore, angioplasty of vulnerable plaques is high risk, and may lead to embolism of the artery tree post surgery. Thus imaging of this sub type of plaques may help reduce post-surgical complication.

A seventh aspect of the present invention is the use of the pharmaceutical composition of the invention for the diagnostic imaging of inflammatory disease and in particular the diagnostic imaging of COPD.

BRIEF DESCRIPTION OF THE FIGURES

FIG. 8 also illustrates the results of the autoradiography (labeled "Autorad") carried out on samples of left carotid artery taken from the ApoE(−/−) mice after in vivo injection of Compound 5.

EXAMPLES

Figure 1:
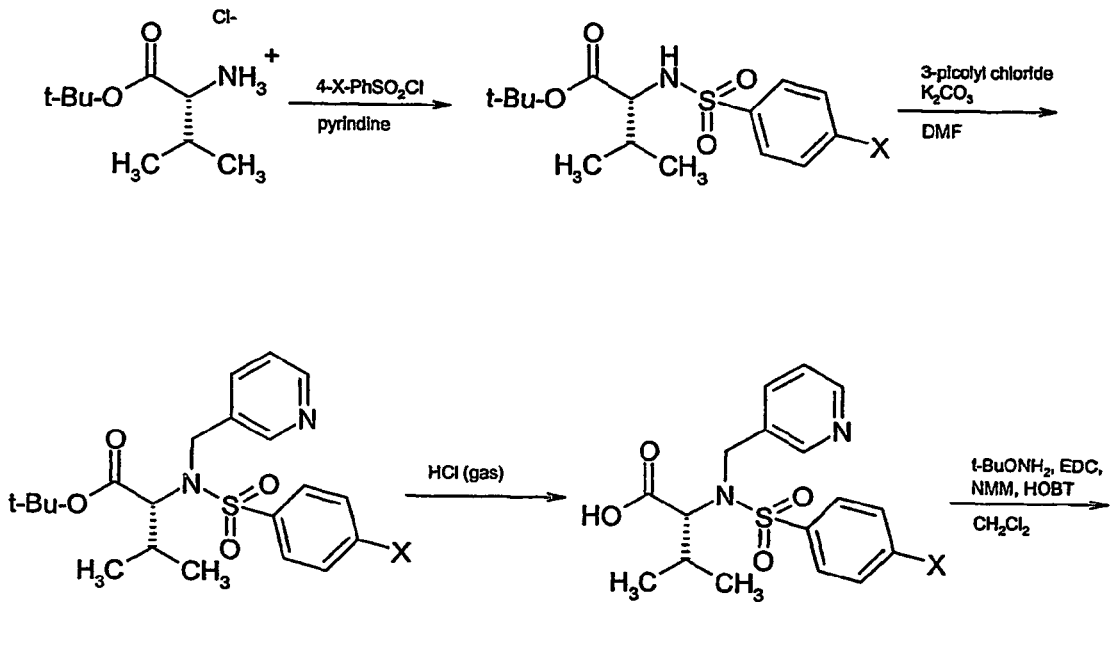
FIG. 1 illustrates the synthetic route that was used to prepare precursor compounds for the radiosynthesis of diagnostic imaging agents of the invention where the γ-emitting radionuclide is a radioactive isotope of iodine. Non-radioactive versions of these radioiodinated diagnostic imaging agents were also prepared via this synthetic route. "X" in FIG. 1 is as defined for Formulae V and VI therein.
Figure 1:
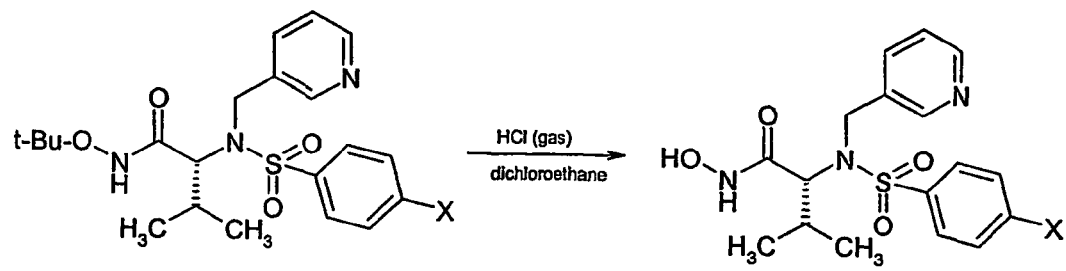
Figure 1:
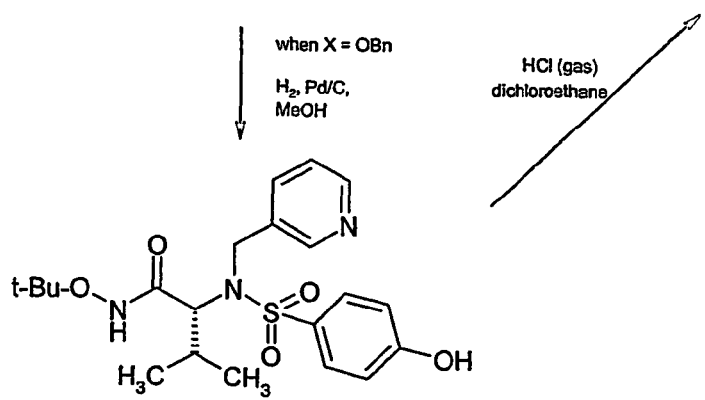

Example 1 describes the synthetic route that was used to prepare the non-radioactive prior art compound CGS 27023.

Example 2 describes the synthetic route that was used to prepare Compound 9, a non-radioactive version of Compounds 6 and 7, both of which are diagnostic imaging agents of the invention.

Example 3 describes the synthetic route that was used to prepare Compound 14, which is the precursor used for the preparation of Compounds 6 and 7 as described in Examples 14 and 15.

Example 4 describes the synthetic route that was used to prepare Compound 13, which is the precursor used for the preparation of Compounds 4 and 5 as described in Examples 12 and 13.

Example 5 describes the synthetic route used for the synthesis of Compound 8, which is a non-radioactive version of Compounds 4 and 5, both of which are diagnostic imaging agents of the invention.

Example 6 describes the synthesis used for the preparation of CA1, the chelating agent used to co-ordinate $^{99m}$Tc in Compounds 1, 2, 3, 16 and 17, all of which are diagnostic imaging agents of the invention.

Example 7 describes the synthetic route that was used for the synthesis of Compound 10, a ligand conjugate that can be labelled with $^{99m}$Tc to produce Compound 1.

Example 8 describes the synthetic route that was used to prepare Compound 11, a ligand conjugate that can be labelled with $^{99m}$Tc to produce Compound 2.

Example 9 describes the synthetic route that was used to prepare Compound 18, a ligand conjugate that can be labelled with $^{99m}$Tc to produce Compound 16.

Example 10 describes the synthetic route that was used to prepare Compound 19, a ligand conjugate that can be labelled with $^{99m}$Tc to produce Compound 17.

Example 11 describes a method of labelling compounds 10, 11, 12, 18 and 19 with $^{99m}$Tc.

Example 12 describes the preparation of Compound 4 by labelling Compound 13 with $^{123}$I. Example 13 refers to Example 12 as the same method of preparation was used to obtain Compound 5, although the labelling of Compound 13 was with $^{125}$I in the latter case.

Example 14 describes the radiosynthesis of Compound 6 using the precursor Compound 14. Example 15 refers to Example 14 as the same radiosynthesis was used to prepare Compound 7. Both Compounds 6 and 7 are diagnostic imaging agents of the invention.

Example 16 describes the synthesis of Compound 15, which is a precursor suitable for the radiosynthesis of Compounds 6 and 7.

Example 17 describes the radiosynthesis of Compound 7 from the tributyltin precursor Compound 15.

Example 18 describes the assay that was used to evaluate the capacity of the compounds of the invention to inhibit MMP-2 and MMP-9. The results in Table 2 show that non-radioactive versions of the diagnostic imaging agents of the invention (Compounds 8 and 9) have MMP inhibitory activity that is comparable to the prior art compound. This provides evidence that the radioactive versions of these compounds (Compounds 2-5) can be used as diagnostic imaging agents in disease states where MMPs are involved.

Example 19 describes the ApoE(−/−) mouse model that was used to evaluate the in vivo characteristics of the compounds of the invention.

Example 20 describes the method used to prepare tissue samples for histology and immunohistochemistry. Example 21 describes the method used to prepare samples for autoradiography. The results of these experiments, shown in FIG. 8, demonstrate that Compound 5 uptake correlates with the presence of MMP-9.

Example 22 describes how in vivo imaging studies were carried out in mice. The experiments demonstrated that there was increasing uptake of Compound 4 in the area of ligation over 120 minutes, suggesting specific uptake of Compound 4 into the lesion.

Figure 12:
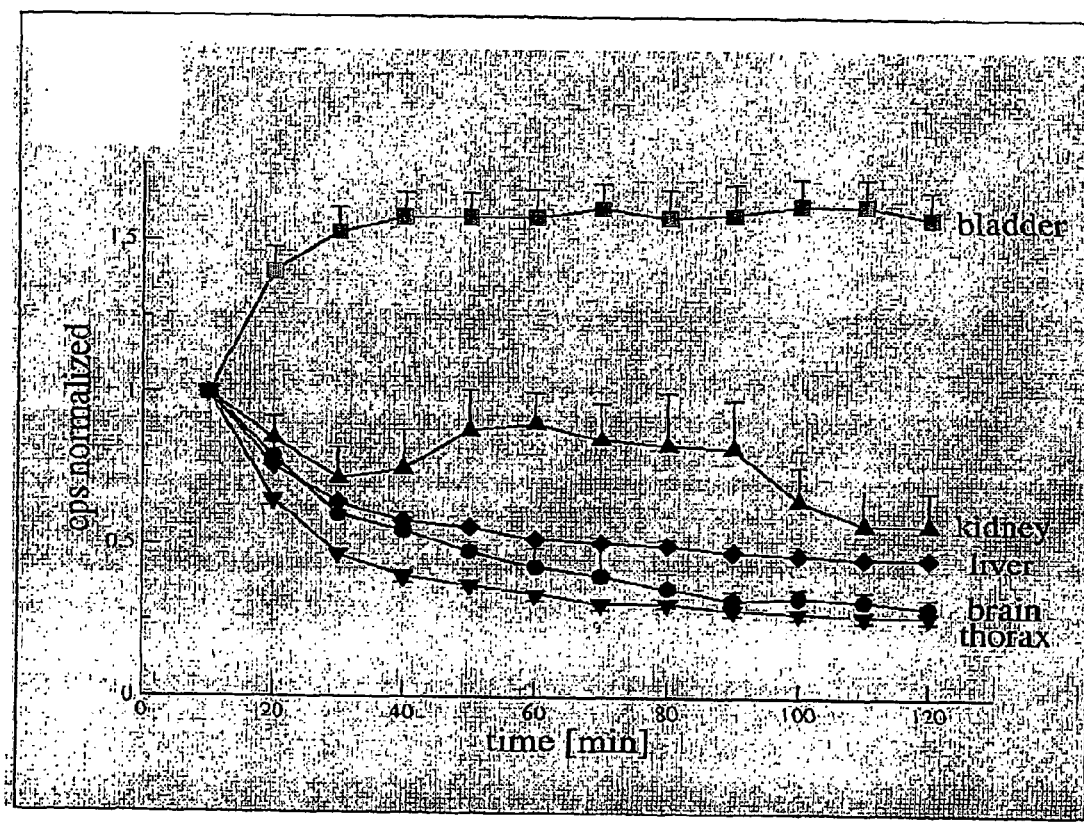
FIG. 12 illustrates mean (±SEM) data obtained from region of interest analysis of liver, kidneys, bladder, brain and thorax of ApoE−/− mice 1-6 in Experiment A.

It was also demonstrated that Compound 4 was not taken up as well in ApoE −/− mice that had been pre-dosed with the non-radioactive prior art compound CGS 27023, suggesting that Compound 4 has similar binding characteristics to CGS 27023. Biodistribution of Compound 4, studied by region of interest analysis, revealed fast clearance from the blood via renal and hepatic excretion and no appreciable signal in the thoracal cavity and brain in the same time period (FIG. 12). Such clearance characteristics are suitable for a diagnostic imaging agent.

Many of the exemplified compounds herein are compounds of Formula I and are defined for convenience in Table 1 on the following page:

TABLE 1

Compounds of Formula I described in the specification

| Compound | $R^1$ | $R^2$ | $R^3$ | $R^4$ |
|---|---|---|---|---|
| CGS27023 (prior art) | isopropyl | 4-OMe | H | 3-pyridyl |
| 1 | isopropyl | 4-CO-CA1-$^{99m}$Tc | H | 3-pyridyl |
| 2 | isopropyl | 4-OMe | H | benzoyl-CA1-$^{99m}$Tc |
| 3 | CH$_2$CH$_2$CO-CA1-$^{99m}$Tc | 4-iodo | H | 3-pyridyl |
| 4 | isopropyl | 4-OH | 3-[$^{123}$I]-iodo | 3-pyridyl |
| 5 | isopropyl. | 4-OH | 3-[$^{125}$I]-iodo | 3-pyridyl |
| 6 | isopropyl | 4-[$^{125}$I]-iodo | H | 3-pyridyl |
| 7 | isopropyl | 4-[$^{123}$I]-iodo | H | 3-pyridyl |
| 8 | isopropyl | 4-OH | 3-iodo | 3-pyridyl |
| 9 | isopropyl | 4-iodo | H | 3-pyridyl |
| 10 | isopropyl | 4-CO-CA1 | H | 3-pyridyl |
| 11 | isopropyl | 4-OMe | H | benzoyl-CA1 |
| 12 | CH$_2$CH$_2$CO-CA1 | 4-iodo | H | 3-pyridyl |
| 13 | isopropyl | 4-OH | H | 3-pyridyl |
| 14 | isopropyl | 4-Br | H | 3-pyridyl |
| 15 | isopropyl | 4-tributyltin | H | 3-pyridyl |
| 16 | isopropyl | 4-OMe | H | Linker 1-CA1-$^{99m}$Tc* |
| 17 | isopropyl | 4-OMe | H | Linker 2-CA1-$^{99m}$Tc* |
| 18 | isopropyl | 4-OMe | H | Linker 1-CA1 |
| 19 | isopropyl | 4-OMe | H | Linker 2-CA1 |
| 20 | isopropyl | 4-(4-[$^{123}$I]iodo-benzamido) | H | 3-pyridyl |

TABLE 1-continued

Compounds of Formula I described in the specification

| Compound | R$^1$ | R$^2$ | R$^3$ | R$^4$ |
|---|---|---|---|---|
| 21 | 4-hydroxy-3-[$^{123}$I]i-odobenzyl | 4-iodo | H | 3-pyridyl |

*Linker 1 = -Ph-C(=O)—NH—(CH$_2$)$_2$—O—(CH$_2$)$_2$—O—(CH$_2$)$_2$—O—(CH$_2$)$_2$—NH—C(=O)—(CH$_2$)$_3$—C(=O)—
Linker 2 = -Ph-C(=O)—NH—(CH$_2$)$_2$—O—(CH$_2$)$_2$—O—(CH$_2$)$_2$—O—(CH$_2$)$_2$—NH—C(=O)—CH$_2$—O—CH$_2$—C(=O)—

Example 1

Preparation of CGS 27023 (Prior Art)

CGS 27023 was synthesised by a modified version of the synthesis described by MacPherson et al [J. Med. Chem. 1997, 40; 2525-2532].

The present synthesis began by reacting commercially available valine t-butyl ester with phenylsulfonyl chloride whereas MacPherson et al start by reacting unprotected valine with phenylsulfonyl chloride, and then protecting the acid functionality as a t-butyl ester. The rest of the present synthesis was the same as that reported by MacPherson et al. FIG. 1 illustrates the synthetic route used, with X=methoxy in the case of CGS 27023.

yield 94% mp 156-158°

$^1$H-NMR (300 MHz, DMSO-D$_6$): δ [ppm]: 10.76 (broad, s, 1 H, OH), 8.52 (m, 2 H, H$_{Aryl}$), 8.18 (d, $^3$J=8.1 Hz, 1 H, H$_{Aryl}$), 7.69 (dd, $^3$J$_1$=8.1 Hz, $^3$J$_2$=5.6 Hz, 1 H, H$_{Aryl}$), 7.47 (d, $^3$J=8.9 Hz, 2 H, H$_{Aryl}$), 6.82 (d, $^3$J=8.9 Hz, 2 H, H$_{Aryl}$), 4.72 (d, $^2$J=16.7 Hz, 1 H, CH$_2$), 4.52 (d, $^2$J=16.7 Hz, 1 H, CH$_2$), 3.63 (s, 3 H, OCH$_3$), 3.64 (d, $^3$J=10.4 Hz, 1 H, N—CH), 1.85-1.71 (m, 1 H, CH(CH$_3$)$_2$), 0.59 (d, $^3$J=6.5 Hz, 3 H, CH(CH$_3$)$_2$), 0.42 (d, $^3$J=6.5 Hz, 3 H, CH(CH$_3$)$_2$).

$^{13}$C-NMR (75.5 MHz, DMSO-$_6$): δ [ppm]: 166.22, 163.01, 144.91, 142.01, 141.14, 138.78, 131.48, 129.59, 126.52, 114.72, 63.35, 56.12, 45.04, 28.09, 19.60, 19.29.

Example 2

Preparation of Compound 9

Compound 9 was prepared by the same method as described for CGS 27023 in Example 1 with X=I in FIG. 1.

yield: 56% of the crude product, which can be recrystallized from acetonitrile to give 36% of a colourless solid.

mp 169° C.

$^1$H-NMR (400 MHz, DMSO-D$_6$): δ [ppm]: 10.87 (broad, s, 1 H, OH), 8.80 (m, 2 H, H$_{Aryl}$), 8.45 (d, $^3$J=8.3 Hz, 1 H, H$_{Aryl}$), 7.96 (dd, $^3$J$_1$=8.1 Hz, $^3$J$_2$=6.0 Hz, 1 H, H$_{Aryl}$), 7.90 (d, $^3$J=8.6 Hz, 2 H, H$_{Aryl}$), 7.52 (d, $^3$J=8.6 Hz, 2 H, H$_{Aryl}$), 4.95 (d, $^2$J=16.9 Hz, 1 H, CH$_2$), 4.74 (d, $^2$J=16.9 Hz, 1 H, CH$_2$), 3.83 (d, $^3$J=10.6 Hz, 1 H, N—CH), 2.05-1.93 (m, 1 H, CH(CH$_3$)$_2$), 0.78 (d, $^3$J=6.5 Hz, 3 H, CH(CH$_3$)$_2$), 0.59 (d, $^3$J=6.5 Hz, 3 H, CH(CH$_3$)$_2$).

$^{13}$C-NMR (75.5 MHz, DMSO-D$_6$): δ [ppm]: 166.95, 145.87, 143.58, 142.69, 140.27, 139.47, 139.18, 129.96, 127.45, 102.99, 64.51, 46.16, 29.11, 20.51, 20.24.

MALDI-TOF: 490 (M-HCl+H$^+$).

Anal. Calcd for C$_{17}$H$_{21}$ICIN$_3$O$_4$S: C 38.83, H 4.03, N 7.99. Found: C, 38.67, H, 3.85, N, 7.94.

Example 3

Preparation of Compound 14

Compound 14 was prepared by the same method as described for CGS 27023 In Example 1 with X=Br in FIG. 1.

yield: 51% of a colourless solid.

mp: 169-170° C.

$^1$H-NMR (300 MHz, DMSO-D$_6$): δ [ppm]: 11.03 (broad, s, 1 H, OH), 8.80 (m, 2 H, H$_{Aryl}$), 8.42 (d, $^3$J=8.1 Hz, 1 H, H$_{Aryl}$), 7.93 (dd, $^3$J$_1$=8.0 Hz, $^3$J$_2$=5.9 Hz, 1 H, H$_{Aryl}$), 7.90 (d, $^3$J=8.6 Hz, 2 H, H$_{Aryl}$), 7.52 (d, $^3$J=8.6 Hz, 2 H, H$_{Aryl}$), 4.98 (d, $^2$J=16.6 Hz, 1 H, CH$_2$), 4.77 (d, $^2$J=16.6 Hz, 1 H, CH$_2$), 3.88 (d, $^3$J=10.5 Hz, 1 H, N—CH), 2.08-1.95 (m, 1 H, CH(CH$_3$)$_2$), 0.81 (d, $^3$J=6.5 Hz, 3 H, CH(CH$_3$)$_2$), 0.63 (d, $^3$J=6.5 Hz, 3 H, CH(CH$_3$)$_2$).

$^{13}$C-NMR (75.5 MHz, DMSO-D$_6$): δ [ppm]: 165.91, 145.13, 142.02, 141.17, 138.91, 138.47, 132.67, 129.39, 127.51, 126.66, 63.54, 45.18, 28.12, 19.51, 19.23.

MALDI-TOF: 466 (M-HCl+Na$^+$), 464 (M-HCl+Na$^+$), 444 (M-HCl+H$^+$), 442 (M-HCl+H$^+$).

Anal. Calcd for C$_{17}$H$_{21}$BrClN$_3$O$_4$S: C, 42.84, H, 4.42, N, 8.78. Found C, 42.68, H, 4.20, N, 8.52.

Example 4

Preparation of Compound 13

The synthesis of Compound 13 was carried out via the same route as for CGS 27023 described in Example 1 up to Formula V of FIG. 1 with X=BnO (N-(tert-Butyloxy)-2(R)-[[(4-benzyloxyphenyl)sulfonyl](3-picolyl)amino]-3-methylbutanamide).

1.20 g (2.28 mmol) of the compound corresponding to Formula V of FIG. 1 where X=BnO was dissolved in 30 ml abs. methanol, treated with 111 mg Pd/C (10%) and stirred for 66 h under an H$_2$-atmosphere. The catalyst was filtered off and washed with 80 ml methanol. The solvent was evaporated and the solid residue was dried in vacuum. Recrystallization from chloroform yielded 797 mg (1.83 mmol, 80%) of the colourless fine-crystalline product, Formula V of FIG. 1 where X=OH (N-(tert-Butyloxy)-2(R)-[[(4-hydroxyphenyl)sulfonyl](3-picolyl)amino]-3methyl-butanamide).

mp 160-162° C.

$^1$H-NMR (300 MHz, DMSO-D$_6$): δ [ppm]: 10.74 (s, 1 H, OH), 8.64 (s, 1 H, H$_{Aryl}$), 8.54 (m, 1 H, H$_{Aryl}$), 7.83 (d, $^3$J=7.9 Hz, 1 H, H$_{Aryl}$), 7.63 (d, $^3$J=8.7 Hz, 2 H, H$_{Aryl}$), 7.37 (dd, $^3$J$_1$=7.8 Hz, $^3$J$_2$=4.8 Hz, 1 H, H$_{Aryl}$), 6.91 (d, $^3$J=8.7 Hz, 2 H, H$_{Aryl}$), 4.80 (s, 2 H, CH$_2$), 4.09 (d, $^3$J=10.6 Hz, 1 H, N—CH), 2.09-1.97 (m, 1 H, CH(CH$_3$)$_2$), 1.22 (s, 9 H, C(CH$_3$)$_3$), 0.93 (d, $^3$J=6.3 Hz, 3 H, CH(CH$_3$)$_2$), 0.86 (d, $^3$J=6.3 Hz, 3 H, CH(CH$_3$)$_2$).

$^{13}$C-NMR (75.5 MHz, DMSO-D$_6$): δ [ppm]: 168.14, 161.56, 150.30, 148.49, 136.64, 133.85, 130.87, 129.43, 123.18, 115.78, 81.04, 63.07, 45.52, 28.56, 26.60, 19.59, 19.20.

MALDI-TOF: 474 (M+K$^+$), 458 (M+Na$^+$), 436 (M+H$^+$).

600 mg (1.38 mmol) Formula V of FIG. 1 where X=OH was dissolved in 30 ml dichloroethane containing 80 μl (1.38 mmol) ethanol. The solution was cooled to −10° C. and hydrochloric acid was bubbled through for 3 h. The reaction vessel was sealed and the mixture allowed to warm to RT. After stirring for 2 days the solvent was reduced to ⅓ volume by evaporation and the residue was treated with ether. The resulting suspension was stirred vigorously for 4 h. The precipitate was collected by suction filtration and dried in vacuo to provide 562 mg (1.35 mmol, 98%) Compound 13 as a colourless powdery solid.

$^1$H-NMR (300 MHz, DMSO-D$_6$): δ [ppm]: 11.13 (s, 1 H, OH), 10.83 (s, 1 H, OH), 8.96 (s, 2 H, H$_{Aryl}$), 8.59 (d, $^3$J=8.0

Hz, 1 H, H$_{Aryl}$), 8.11 (dd, $^3$J$_1$=7.7 Hz, $^3$J$_2$=5.9 Hz, 1 H, H$_{Aryl}$) 7.77 (d, $^3$J=8.6 Hz, 2 H, H$_{Aryl}$), 7.06 (d, $^3$J=8.6 Hz, 2 H, H$_{Aryl}$), 5.11 (d, $^2$J=16.8 Hz, 1 H, CH$_2$), 4.90 (d, $^2$J=16.8 Hz, 1 H, CH$_2$), 4.01 (d, $^3$J=10.6 Hz, 1 H, N—CH), 2.25-2.12 (m, 1 H, CH(CH$_3$)$_2$), 0.99 (d, $^3$J=6.4 Hz, 3 H, CH(CH$_3$)$_2$), 0.81 (d, $^3$J=6.4 Hz, 3 H, CH(CH$_3$)$_2$).

$^{13}$C-NMR (75.5 MHz, DMSO-D$_6$): δ [ppm]: 166.32, 162.04, 144.85, 142.09, 141.17, 138.99, 129.72, 129.59, 126.45, 115.93, 63.30, 44.98, 28.08, 19.49, 19.33.

MALDI-TOF: 402 (M-HCl+Na)$^+$.

Example 5

Preparation of Compound 8

The synthesis of Compound 8 was carried out via the same route as for CGS27023 described in Example 1 up to Formula V of FIG. 1, X=OH (N-(tert-Butyloxy)-2(R)-[[(4-hydroxyphenyl)sulfonyl](3-picolyl)amino]3-methyl-butanamide).

1.00 g (2.30 mmol) of Formula V of FIG. 1 where X=OH was dissolved in 40 ml methanol and treated with 1.22 g (11.5 mmol) sodium carbonate. The solution was cooled in an ice bath and 2.3 ml of a 1M solution of iodine monochloride in methanol was added dropwise over a period of 1 h. During the addition the deep red color of the solution disappeared almost instantly. The mixture was allowed to come to RT and stirred overnight. Afterwards the suspension was filtered, the filtrate was treated with 4 ml 10% sodium thiosulfate solution and adjusted to pH 7 with 1 N H$_2$SO$_4$. After extraction with ether the combined extracts were washed with brine and dried (Na$_2$SO$_4$). The ether solution was concentrated in vacuo to give 900 mg of N-(tert-Butyloxy)-2(R)-[[(4-hydroxy-3-iodophenyl)sulfonyl](3-picolyl)-amino]-3-methylbutanamide. This was a slight pink solid, which was used in the next step without further purification.

900 mg of the crude N-(tert-Butyloxy)-2(R)-[[(4-hydroxy-3-iodophenyl)sulfonyl](3-picolyl)-amino]-3-methylbutanamide was dissolved in 150 ml dichloromethane containing 93 μl ethanol. The solution was cooled to −10° C. and hydrochloric acid was bubbled through for 1.5 h. The reaction vessel was sealed and the mixture was allowed to warm up to RT. After stirring for 19 h at RT, the solvent was reduced to a volume of approximately 20 ml by evaporation and the residue was treated with ca. 50 ml ether. The resulting suspension was stirred vigorously for 1-2 h. The precipitate was collected by suction filtration and dried in vacuo to provide 830 mg of a colourless to slight yellow powdery solid. Twofold recrystallization from methanol/acetonitrile (1:1) yields 150 mg of the pure Compound 8.

yield: 12% (over two steps).

mp: 201-203° C.

$^1$H-NMR (300 MHz, DMSO-D$_6$): δ [ppm]: 11.70 (broad, s, 1 H, OH), 11.03 (broad, s, 1 H, OH), 8.86 (s, 1 H, H$_{Aryl}$), 8.84 (s, 1 H, H$_{Aryl}$), 8.45 (d, $^3$J=8.1 Hz, 1 H, H$_{Aryl}$), 7.98 (dd, $^3$J$_1$=8.3 Hz, $^3$J$_2$=5.7 Hz, 1 H, H$_{Aryl}$), 7.96 (d, $^3$J=2.3 Hz, 1 H, H$_{Aryl}$), 7.69 (d, $^3$J=8.6 Hz, 1 H, H$_{Aryl}$), 7.10 (d, $^3$J=8.6 Hz, 1 H, H$_{Aryl}$), 4.98 (d, $^2$J=16.5 Hz, 1 H, CH$_2$), 4.82 (d, $^2$J=16.5 Hz, 1 H, CH$_2$), 3.89 (d, $^3$J=10.6 Hz, 1 H, N—CH), 2.15-2.02 (m, 1 H, CH(CH$_3$)$_2$), 0.87 (d, $^3$J=6.6 Hz, 3 H, CH(CH$_3$)$_2$), 0.69 (d, $^3$J=6.6 Hz, 3 H, CH(CH$_3$)$_2$).

$^{13}$C-NMR (75.5 MHz, DMSO-D$_6$): δ [ppm]: 166.25, 161.32, 144.95, 142.22, 141.36, 138.72, 138.12, 131.33, 129.15, 126.44, 115.16, 84.87, 63.33, 45.03, 28.05, 19.50, 19.31.

Anal. Calcd. for C$_{17}$H$_{21}$IN$_3$O$_5$SCl: C, 37.69, H, 3.90, N, 7.76. found: C, 37.84, H, 4.42, N, 7.39.

Example 6

Preparation of Chelating Agent 1

6(a) 3(methoxycarbonylmethylene)glutaric acid dimethylester

Carbomethoxymethylenetriphenylphosphorane (167 g, 0.5 mol) in toluene (600 ml) was treated with dimethyl 3-oxoglutarate (87 g, 0.5 mol) and the reaction heated to 100° C. on an oil bath at 120° C. under an atmosphere of nitrogen for 36 h. The reaction was then concentrated in vacuo and the oily residue triturated with 40/60 petrol ether/diethylether 1:1, 600 ml. Triphenylphosphine oxide precipitated out and the supernatant liquid was decanted/filtered off. The residue on evaporation in vacuo was Kugelrohr distilled under high vacuum Bpt (oven temperature 180-200° C. at 0.2 torr) to give 3(methoxycarbonylmethylene)glutaric acid dimethylester in 89.08 g, 267 mM, 53%.

NMR $^1$H(CDCl$_3$): δ 3.31 (2H, s, CH$_2$), 3.7(9H, s, 3×OCH$_3$), 3.87 (2H, s, CH$_2$), 5.79 (1H, s, =CH) ppm.

NMR $^{13}$C(CDCl$_3$), δ 36.56,CH$_3$, 48.7, 2×CH$_3$, 52.09 and 52.5 (2×CH$_2$); 122.3 and 146.16 C=CH; 165.9, 170.0 and 170.5 3×COO ppm.

6(b) Hydrogenation of 3-(methoxycarbonylmethylene)glutaric acid dimethylester

3(methoxycarbonylmethylene)glutaric acid dimethylester (89 g, 267 mmol) in methanol (200 ml) was shaken with (10% palladium on charcoal: 50% water) (9 g) under an atmosphere of hydrogen gas (50 psi) for (30 h). The solution was filtered through kieselguhr and concentrated in vacuo to give 3-(methoxycarbonylmethyl)glutaric acid dimethylester as an oil yield (84.9 g, 94%).

NMR $^1$H(CDCl$_3$), δ 2.48 (6H, d, J=8 Hz, 3×CH$_2$), 2.78 (1H, hextet, J=8 Hz CH) 3.7 (9H, s, 3×CH$_3$).

NMR $^{13}$C(CDCl$_3$), δ 28.6, CH; 37.50, 3×CH$_3$; 51.6, 3×CH$_2$; 172.28,3×COO

6(c) Reduction and Esterification of Trimethyl Ester to the Triacetate

Under an atmosphere of nitrogen in a 3 necked 2 L round bottomed flask lithium aluminium hydride (20 g, 588 mmol) in tetrahydrofuran (400 ml) was treated cautiously with tri (methyloxycarbonylmethyl)methane (40 g, 212 mmol) in tetrahydrofuran (200 ml) over 1 h. A strongly exothermic reaction occurred, causing the solvent to reflux strongly. The reaction was heated on an oil bath at 90° C. at reflux for 3 days. The reaction was quenched by the cautious dropwise addition of acetic acid (100 ml) until the evolution of hydrogen ceased. The stirred reaction mixture was cautiously treated with acetic anhydride solution (500 ml) at such a rate as to cause gentle reflux. The flask was equipped for distillation and stirred and then heating at 90° C. (oil bath temperature) to distil out the tetrahydrofuran. A further portion of acetic anhydride (300 ml) was added, the reaction returned to reflux configuration and stirred and heated in an oil bath at 140° C. for 5 h. The reaction was allowed to cool and filtered. The aluminium oxide precipitate was washed with ethyl acetate and the combined filtrates concentrated on a rotary evaporator at a water bath temperature of 50° C. in vacuo (5 mm Hg) to afford an oil. The oil was taken up in ethyl acetate (500 ml) and washed with saturated aqueous potassium carbonate solution. The ethyl acetate solution was separated, dried over sodium sulphate, and concentrated in vacuo to afford an oil. The oil was Kugelrohr distilled in high vacuum to give tris(2-acetoxyethyl)methane (45.313 g, 95.9% yield, 0.165 mol) as an oil. Bp. 220 at 0.1 mmHg.

NMR $^1$H(CDCl$_3$), δ 1.66(7H, m, 3×CH$_2$, CH), 2.08(1H, s, 3×CH$_3$); 4.1(6H, t 3×CH$_2$O).

NMR $^{13}$C(CDCl$_3$), δ 20.9, CH$_3$; 29.34, CH; 32.17, CH$_2$; 62.15, CH$_2$O; 171, CO.

6(d) Removal of Acetate Groups from the Triacetate

Tris(2-acetoxyethyl)methane (45.3 g, 165 mM) in methanol (200 ml) and 880 ammonia (100 ml) was heated on an oil bath at 80° C. for 2 days. The reaction was treated with a further portion of 880 ammonia (50 ml) and heated at 80° C. in an oil bath for 24 h. A further portion of 880 ammonia (50 ml) was added and the reaction heated at 80° C. for 24 h. The reaction was then concentrated in vacuo to remove all solvents to give an oil. This was taken up into 880 ammonia (150 ml) and heated at 80° C. for 24 h. The reaction was then concentrated in vacuo to remove all solvents to give an oil. Kugelrohr distillation gave acetamide bp 170-180 0.2 mm. The bulbs containing the acetamide were washed clean and the distillation continued. Tris(2-hydroxyethyl)methane (22.53 g, 152 mmol, 92.1%) distilled at bp 220° C. 0.2 mm.

NMR $^1$H(CDCl$_3$), δ 1.45(6H, q, 3×CH$_2$), 2.2(1H, quintet, CH); 3.7(6H, t 3×CH$_2$OH); 5.5(3H, brs, 3×OH).

NMR $^{13}$C(CDCl$_3$), δ 22.13, CH; 33.95, 3×CH$_2$; 57.8, 3×CH$_2$OH.

6(e) Conversion of the Triol to the tris(methanesulphonate)

To an stirred ice-cooled solution of tris(2-hydroxyethyl) methane (10 g, 0.0676 mol) in dichloromethane (50 ml) was slowly dripped a solution of methanesulphonyl chloride (40 g, 0.349 mol) in dichloromethane (50 ml) under nitrogen at such a rate that the temperature did not rise above 15° C. Pyridine (21.4 g, 0.27 mol, 4 eq) dissolved in dichloromethane (50 ml) was then added drop-wise at such a rate that the temperature did not rise above 15° C., exothermic reaction. The reaction was left to stir at room temperature for 24 h and then treated with 5N hydrochloric acid solution (80 ml) and the layers separated. The aqueous layer was extracted with further dichloromethane (50 ml) and the organic extracts combined, dried over sodium sulphate, filtered and concentrated in vacuo to give tris(2-(methylsulphonyloxy)ethyl) methane contaminated with excess methanesulphonyl chloride. Theoretical yield was 25.8 g.

NMR $^1$H(CDCl$_3$) δ 4.3 (6H, t, 2×CH$_2$), 3.0 (9H, s, 3×CH$_3$), 2 (1H, hextet, CH), 1.85 (6H, q, 3×CH$_2$).

6(f) Preparation of 1,1,1-tris(2-azidoethyl)methane

A stirred solution of tris(2-(methylsulphonyloxy)-ethyl) methane [from step 1(e), contaminated with excess methylsulphonyl chloride] (25.8 g, 67 mmol, theoretical) in dry DMF (250 ml) under nitrogen was treated with sodium azide (30.7 g, 0.47 mol) portion-wise over 15 minutes. An exotherm was observed and the reaction was cooled on an ice bath. After 30 minutes, the reaction mixture was heated on an oil bath at 50° C. for 24 h. The reaction became brown in colour. The reaction was allowed to cool, treated with dilute potassium carbonate solution (200 ml) and extracted three times with 40/60 petrol ether/diethylether 10:1 (3×150 ml). The organic extracts were washed with water (2×150 ml), dried over sodium sulphate and filtered. Ethanol (200 ml) was added to the petrol/ether solution to keep the triazide in solution and the volume reduced in vacuo to no less than 200 ml.

Ethanol (200 ml) was added and reconcentrated in vacuo to remove the last traces of petrol leaving no less than 200 ml of ethanolic solution.

CARE: DO NOT REMOVE ALL THE SOLVENT AS THE AZIDE IS POTENTIALLY EXPLOSIVE AND SHOULD BE KEPT IN DILUTE SOLUTION AT ALL TIMES.

NMR $^1$H(CDCl$_3$), δ 3.35 (6H, t, 3×CH$_2$), 1.8 (1H, hextet, CH), 1.6 (6H, q, 3×CH$_2$).

6(g) Preparation of 1,1,1-tris(2-aminoethyl)methane

Tris(2-azidoethyl)methane (15.06 g, 0.0676 mol), (assuming 100% yield from previous reaction) in ethanol (200 ml) was treated with 10% palladium on charcoal (2 g, 50% water) and hydrogenated for 12 h. The reaction vessel was evacuated every 2 hours to remove nitrogen evolved from the reaction and refilled with hydrogen. A sample was taken for NMR analysis to confirm complete conversion of the triazide to the triamine.

CAUTION: UNREDUCED AZIDE COULD EXPLODE ON DISTILLATION.

The reaction was filtered through a celite pad to remove the catalyst and concentrated in vacuo to give tris(2-aminoethyl) methane as an oil. This was further purified by Kugelrohr distillation bp. 180-200° C. at 0.4 mm/Hg to give a colourless oil (8.1 g, 55.9 mmol, 82.7% overall yield from the triol).

NMR $^1$H(CDCl$_3$), 2.72 (6H, t, 3×CH$_2$N), 1.41 (H, septet, CH), 1.39 (6H, q, 3×CH$_2$).

NMR $^{13}$C(CDCl$_3$), δ 39.8 (CH$_2$NH$_2$), 38.2 (CH$_2$.), 31.0 (CH).

1,1,1-tris(2-aminoethyl)methane can also prepared by the alternative method given below:

6(g)(l): Amidation of trimethylester with p-methoxy-benzylamine

Tris(methyloxycarbonylmethyl)methane [2 g, 8.4 mmol; prepared as in Step 6(b) above] was dissolved in p-methoxy-benzylamine (25 g, 178.6 mmol). The apparatus was set up for distillation and heated to 120° C. for 24 hrs under nitrogen flow. The progress of the reaction was monitored by the amount of methanol collected. The reaction mixture was cooled to ambient temperature and 30 ml of ethyl acetate was added, then the precipitated triamide product stirred for 30 min. The triamide was isolated by filtration and the filter cake washed several times with sufficient amounts of ethyl acetate to remove excess p-methoxy-benzylamine. After drying 4.6 g, 100%, of a white powder was obtained. The highly insoluble product was used directly in the next step without further purification or characterisation.

6(g)(ii): Preparation of 1,1,1-tris[2-(p-methoxybenzylamino)ethyl]methane

To a 1000 ml 3-necked round bottomed flask cooled in a ice-water bath the triamide from step 2(a) (10 g, 17.89 mmol) is carefully added to 250 ml of 1M borane solution (3.5 g, 244.3 mmol) borane. After complete addition the ice-water bath is removed and the reaction mixture slowly heated to 60° C. The reaction mixture is stirred at 60° C. for 20 hrs. A sample of the reaction mixture (1 ml) was withdrawn, and mixed with 0.5 ml 5N HCl and left standing for 30 min. To the sample 0.5 ml of 50 NaOH was added, followed by 2 ml of water and the solution was stirred until all of the white precipitate dissolved. The solution was extracted with ether (5 ml) and evaporated. The residue was dissolved in acetonitrile at a concentration of 1 mg/ml and analysed by MS. If mono- and diamide (M+H/z=520 and 534) are seen in the MS spectrum, the reaction is not complete. To complete the reaction, a further 100 ml of 1M borane THF solution is added and the reaction mixture stirred for 6 more hrs at 60° C. and a new sample withdrawn following the previous sampling procedure. Further addition of the 1M borane in THF solution is continued as necessary until there is complete conversion to the triamine.

The reaction mixture is cooled to ambient temperature and 5N HCl is slowly added, [CARE: vigorous foam formation occurs!]. HCl was added until no more gas evolution is observed. The mixture was stirred for 30 min and then evaporated. The cake was suspended in aqueous NaOH solution (20-40%; 1:2 w/v) and stirred for 30 minutes. The mixture was then diluted with water (3 volumes). The mixture was then extracted with diethylether (2×150 ml) [CARE: do not use halogenated solvents]. The combined organic phases were then washed with water (1×200 ml), brine (150 ml) and dried over magnesium sulphate. Yield after evaporation: 7.6 g, 84% as oil.

NMR $^1$H(CDCl$_3$), δ: 1.45, (6H, m, 3×CH$_2$; 1.54, (1H, septet, CH); 2.60 (6H, t, 3×CH$_2$N); 3.68 (6H, s, ArCH$_2$); 3.78 (9H, s, 3×CH$_3$O); 6.94(6H, d, 6×Ar). 7.20(6H, d, 6×Ar).

NMR $^{13}$C(CDCl$_3$), δ: 32.17, CH; 34.44, CH$_2$; 47.00, CH$_2$; 53.56, ArCH$_2$; 55.25, CH$_3$O; 113.78, Ar; 129.29, Ar; 132.61; Ar; 158.60, Ar;

6(g)(iii) Preparation of 1,1,1-tris(2-aminoethyl)methane 1,1,1-tris[2-(p-methoxybenzylamino)ethyl]methane (20.0 gram, 0.036 mol) was dissolved in methanol (100 ml) and Pd(OH)$_2$ (5.0 gram) was added. The mixture was hydrogenated (3 bar, 100° C., in an autoclave) and stirred for 5 hours. Pd(OH)$_2$ was added in two more portions (2×5 gram) after 10 and 15 hours respectively.

The reaction mixture was filtered and the filtrate was washed with methanol. The combined organic phase was evaporated and the residue was distilled under vacuum (1×10$^{-2}$, 110° C.) to give 2.60 gram (50%) of 1,1,1-tris(2-aminoethyl)methane identical to that obtained by the previously described method.

6(h) Preparation of 3-chloro-3-methyl-2-nitrosobutane

A mixture of 2-methylbut-2-ene (147 ml, 1.4 mol) and isoamyl nitrite (156 ml, 1.16 mol) was cooled to −30° C. in a bath of cardice and methanol and vigorously stirred with an overhead air stirrer and treated dropwise with concentrated hydrochloric acid (140 ml, 1.68 mol) at such a rate that the temperature was maintained below −20° C. This requires about 1 h as there is a significant exotherm and care must be taken to prevent overheating. Ethanol (100 ml) was added to reduce the viscosity of the slurry that had formed at the end of the addition and the reaction stirred at −20 to −10° C. for a further 2 h to complete the reaction. The precipitate was collected by filtration under vacuum and washed with 4×30 ml of cold (−20° C.) ethanol and 100 ml of ice cold water, and dried in vacuo to give 3-chloro-3-methyl-2-nitrosobutane as a white solid. The ethanol filtrate and washings were combined and diluted with water (200 ml) and cooled and allowed to stand for 1 h at −10° C. when a further crop of 3-chloro-3-methyl-2-nitrosobutane crystallised out. The precipitate was collected by filtration and washed with the minimum of water and dried in vacuo to give a total yield of 3-chloro-3-methyl-2-nitrosobutane (115 g 0.85 mol, 73%)>98% pure by NMR.

NMR $^1$H(CDCl$_3$), As a mixture of isomers (isomer1, 90%) 1.5 d, (2H, CH$_3$), 1.65 d, (4H, 2×CH$_3$), 5.85,q, and 5.95,q, together 1H. (isomer2, 10%), 1.76 s, (6H, 2×CH$_3$), 2.07(3H, CH$_3$).

6(i) Synthesis of bis[N-(1,1-dimethyl-2-N-hydroxy-imine propyl)2-aminoethyl]-(2-aminoethyl)methane (chelating agent 1)

To a solution of tris(2-aminoethyl)methane (4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (7.56 g, 55.8 mol, 2 eq) was dissolved in dry ethanol (100 ml) and 75 ml of this solution was dripped slowly into the reaction mixture. The reaction was followed by TLC on silica run in dichloromethane, methanol, concentrated (0.88 sg) ammonia; 100/30/5 and the TLC plate developed by spraying with ninhydrin and heating. The mono, di and tri alkylated products were seen with RF's increasing in that order. Analytical HPLC was run using RPR reverse phase column in a gradient of 7.5-75% acetonitrile in 3% aqueous ammonia. The reaction was concentrated in vacuo to remove the ethanol and resuspended in water (110 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mM, 23%).

Mass spec; Positive ion 10 V cone voltage. Found: 344. calculated M+H=344.

NMR $^1$H(CDCl$_3$), δ 1.24(6H, s, 2×CH$_3$), 1.3(6H, s, 2× CH$_3$), 1.25-1.75(7H, m, 3×CH$_2$, CH), (3H, s, 2×CH$_2$), 2.58 (4H, m, CH$_2$N), 2.88(2H, t CH$_2$N$_2$), 5.0 (6H, s, NH$_2$, 2×NH, 2×OH).

NMR $^1$H ((CD$_3$)$_2$SO) δ1.1 4×CH; 1.29, 3×CH$_2$; 2.1 (4H, t, 2×CH$_2$);

NMR $^{13}$C((CD$_3$)SO), δ 9.0 (4×CH$_3$), 25.8 (2×CH$_3$), 31.0 2×CH$_2$, 34.6 CH$_2$, 56.8 2×CH$_2$N; 160.3, C═N.

HPLC conditions: flow rate 8 ml/min using a 25 mm PRP column

A=3% ammonia solution (sp.gr=0.88)/water.

B=Acetonitrlle

| Time | % B |
|---|---|
| 0 | 7.5 |
| 15 | 75.0 |
| 20 | 75.0 |
| 22 | 7.5 |
| 30 | 7.5 |

Load 3 ml of aqueous solution per run, and collect in a time window of 12.5-13.5 min.

Example 7

Preparation of Compound 10

Figure 2:
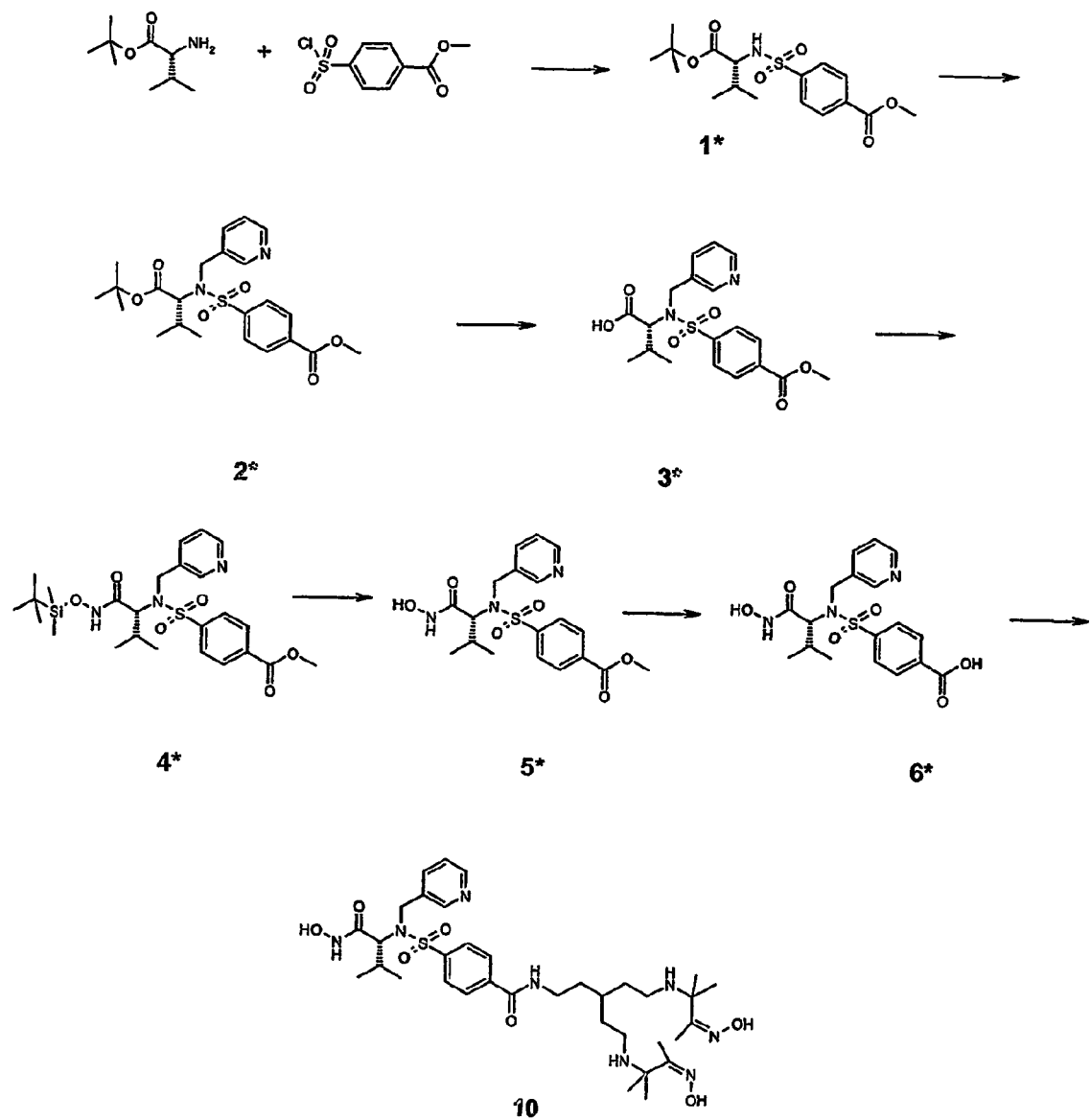
FIGS. 2-5 illustrate the synthetic routes that were used to prepare the ligand conjugates, Compounds 10, 11, 18 and 19, respectively.

The synthetic route is illustrated in FIG. 2.

7(a) 4-(1-tert-butoxycarbonyl-2-methyl-propylsulfamoyl)-benzoic acid methyl ester (Compound 1)

To a stirred suspension of 2-Amino-3-methyl-butyric acid tert-butyl ester (H-D-Val-OtBu.HCl) (500 mg, 2.38 mmol) in acetonitrile (20 ml) was added pyridine (767 µl, 9.52 mmol) at ambient temperature. A clear and colourless solution was quickly obtained. Then a solution of 4-chlorosulfonyl-benzoic acid methyl ester (670 mg, 2.86 mmol) in acetonitrile (6 ml) was added dropwise and the mixture became slightly yellow coloured and was stirred at ambient temperature for 4 hours. The reaction was monitored by TLC (EtOAc/Hexane, 1:1). The solvents were evaporated and ethyl acetate (50 ml) and saturated sodium bicarbonate solution (10 ml) were added. The mixture was transferred into a separatory funnel and vigorously shaken. Then the phases were separated and the ethyl acetate phase was extracted once with brine (10 ml), dried (MgSO4), filtered and evaporated to afford the crude product. Flash chromatography using (Ethyl acetate/Hexane, 1:1) gave the pure product as a white solid. Yield 880 mg (99.55%).

7(b) 4-[(1-tert-butoxycarbonyl-2-methyl-propyl)-pyridin-3-ylmethyl-sulfamoyl]-benzoic acid methyl ester (Compound 2*)

To a stirring solution of 4-(1-tert-Butoxycarbonyl-2-methyl-propylsulfamoyl)-benzoic acid methyl ester (Compound 1*—884 mg, 2.38 mmol) in dimethylformamide (30 ml) at ambient temperature was added cesium carbonate (10.86 g, 33.34 mmol). Then 3-picolyl chloride hydrochloride (546 mg, 3.33 mmol) was added to the suspension and the reaction mixture was stirred at room temperature for 24 hours by which time TLC (EtOAc/Hexane 1:1) monitoring showed the reaction to be completed. The mixture was evaporated to dryness and the residue was stirred in ethyl acetate (50 ml). The ethyl acetate phase was extracted with water (1×50 ml), dried (MgSO4), filtered and evaporated to afford the crude product as a brown oil. This oil was purified by flash chromatography to furnish the pure product as colourless oil. Yield 800 mg (79.21%).

7(c) 4-[(1-carboxy-2-methyl-propyl)-pyridin-3-ylmethyl-sulfamoyl]-benzoic acid methyl ester (Compound 3*)

The ester (Compound 2*—321 mg, 0.75 mmol) was dissolved in methylene chloride (15 ml) and cooled to −10° C. Hydrochloric acid gas was bubbled into the solution for 10 minutes. The reaction mixture was sealed, warmed to room temperature, and stirred for 16 hours. The solvent was evaporated and the residue co-evaporated with methylene chloride (2×10 ml) to afford the product as white foam (278 mg, 83.73% Yield).

7(d) 4-[(1-hydroxycarbamoyl-2-methyl-propyl)-pyridin-3-ylmethyl-sulfamoyl]-benzoic acid methyl ester (Compound 5*)

The acid (Compound 3*—112 mg, 0.28 mmol), 1-hydroxybenzotriazole (39 mg, 0.29 mmol), 4-methylmorpholine (297 µl, 1.4 mmol) and O-tert-butyldimethylsilyl) hydroxylamine (124 mg, 0.84 mmol) were dissolved methylene chloride (8 ml). N-[(dimethylamino)propyl]-N'-ethylcarbodiimide hydrochloride (73 mg, 0.38 mmol) was added and the reaction mixture was stirred for 24 hours. The reaction mixture was diluted with water (10 ml) and extracted with methylene chloride (2×10 ml). The combined methylene chloride phases was dried (Na2SO4), filtered. Some drops of hydrochloric acid in dioxane was added to the filtrate to furnish directly the free hydroxamic acid (108 mg).

7(e) 4-[(1-hydroxycarbamoyl-2-methyl-propyl)-pyridin-3-ylmethyl-sulfamoyl]-benzoic acid (Compound 6*)

2N Sodium hydroxide (200 µl) was added to a solution of the ester (Compound 5*—32 mg, 0.072 mmol), in methanol (1 ml) and the mixture stirred at ambient temperature. After 30 minutes the mixture was evaporated to dryness and the residue dissolved in water (2 ml). The solution was made acidic using 2N HCl. The pure product was obtained after preparatory HPLC as a white powder (28 mg, 95.01%, Yield).

7(f) 4-[(1-hydroxycarbamoyl-2-methyl-propyl)-pyridin-3-ylmethyl-sulfamoyl]-N-{5-(2-hydroxyimino-1,1-dimethyl-propylamino)-3-[2-(2-hydroxyimino-1,1-dimethyl-propylamino)-ethyl]-pentyl}-benzamide (Compound 10)

The acid (Compound 6*)—12.5 mg, 0.031 mmol), 1-hydroxybenzotriazole (3.68 mg, 0.027 mmol), 4-methylmorpholine (17.4 µl, 0.124 mmol) and N-[(dimethylamino)propyl]-N'-ethylcarbodiimide hydrochloride (8.06 mg, 0.042 mmol) were dissolved dimethylformamide (2 ml). Chelating agent 1 (13 mg, 0.037 mmol) was added and the reaction mixture was stirred for 24 hours. After evaporation of the solvents the crude product was applied directly for HPLC purification (Gradient 00_30_60). The product was a slightly brown gum (2 mg, 9% yield).

Example 8

Preparation of Compound 11

Figure 3:
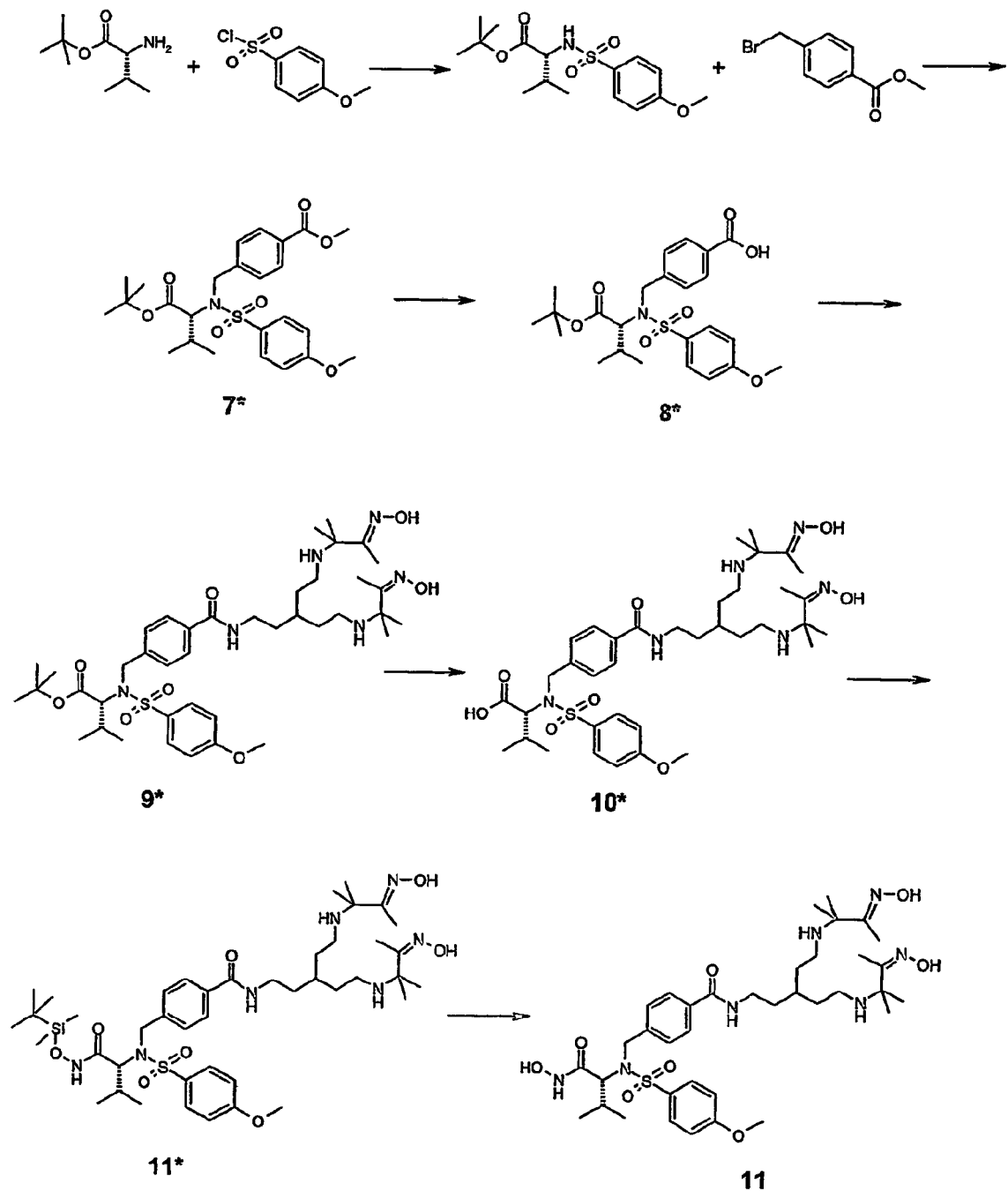
Figure 4:
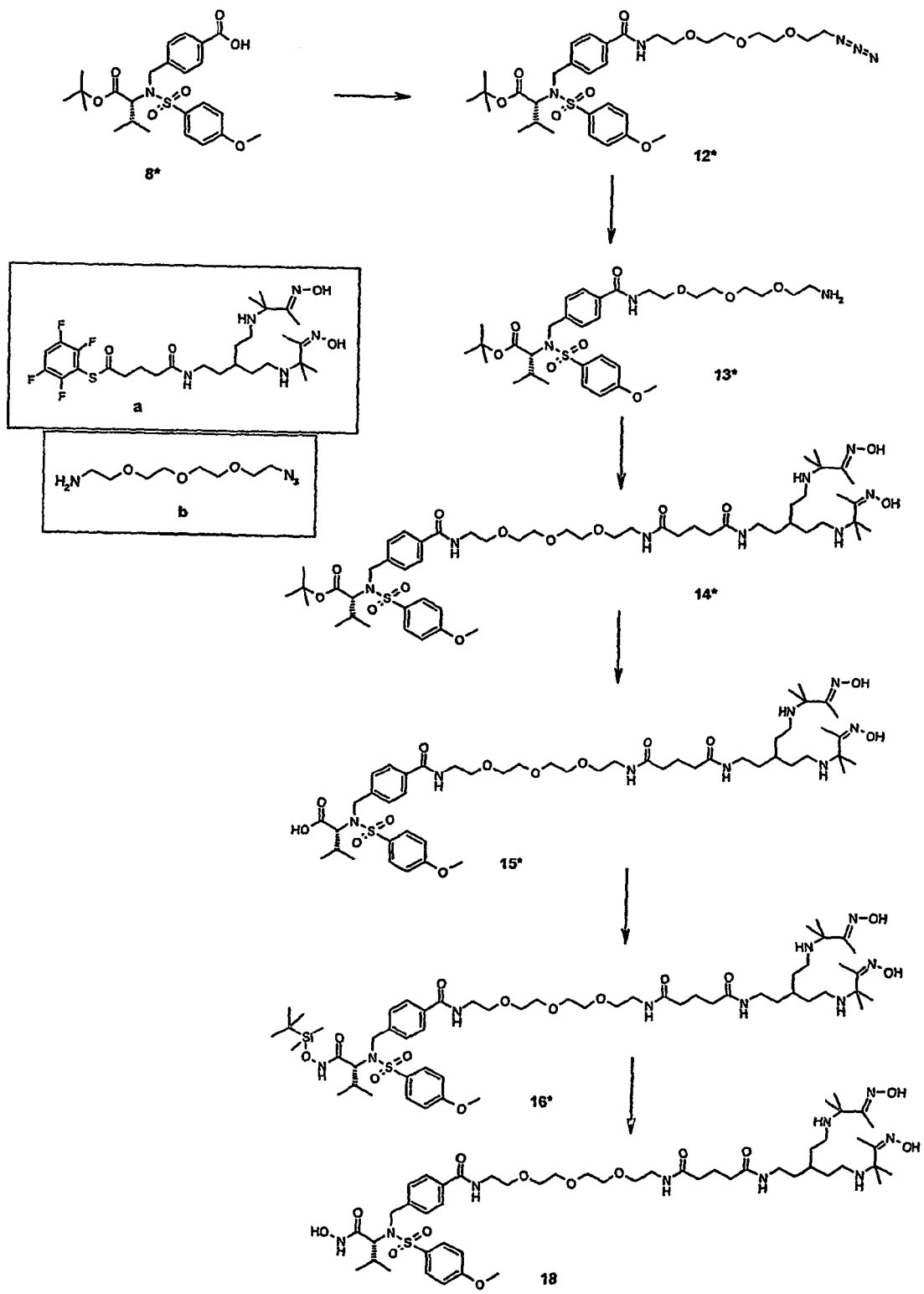
Figure 5:
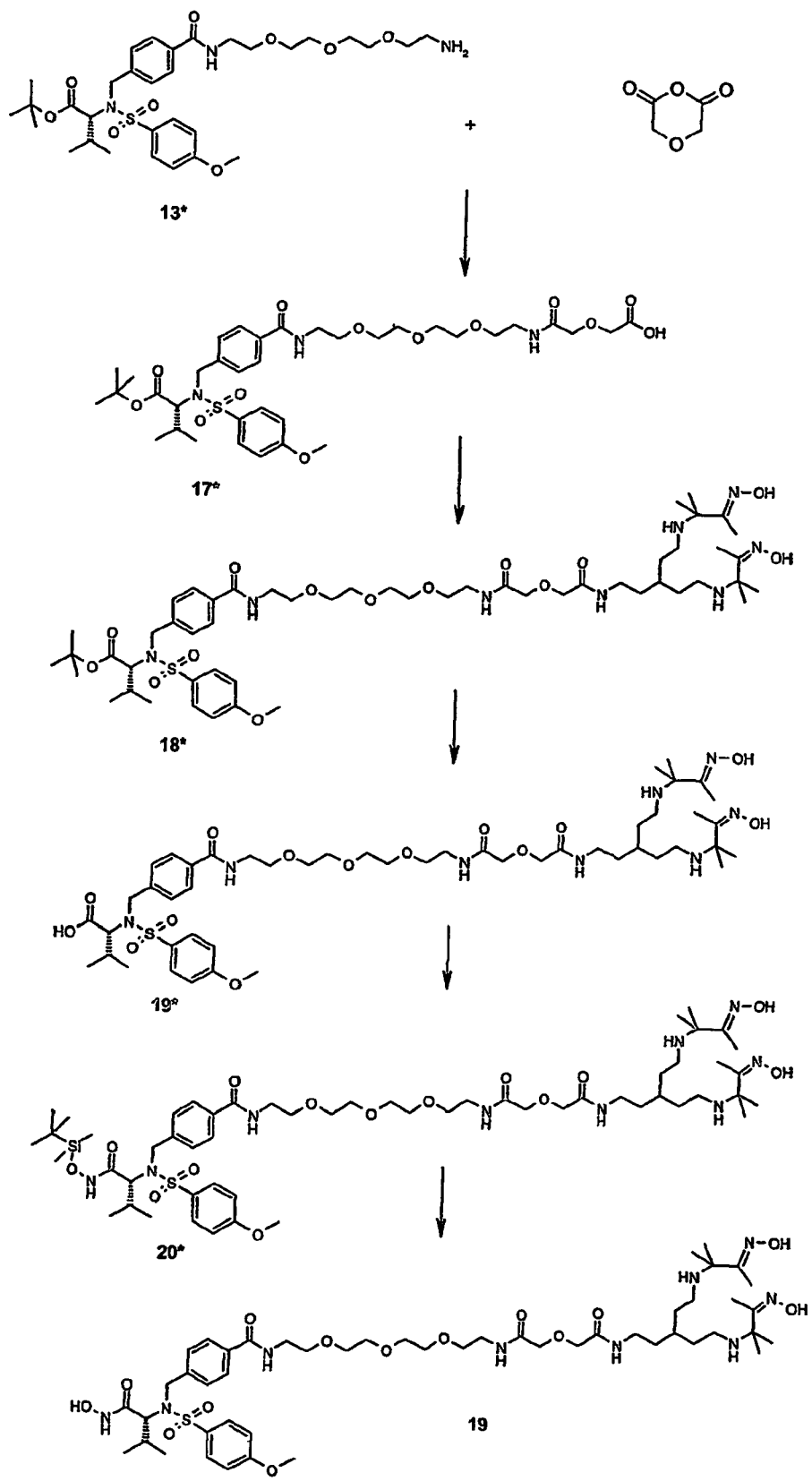

The synthesis of Compound 11 is illustrated in FIG. 3.

8(a) 2-(4-methoxy-benzenesulfonylamino)-3-methyl-butyric acid tert-butyl ester

To a stirred suspension of 2-Amino-3-methyl-butyric acid tert-butyl ester (H-D-Val-OtBu.HCl) (500 mg, 2.38 mmol) in acetonitrile (20 ml) was added pyridine (767 µl, 9.52 mmol) at ambient temperature. A clear and colourless solution was quickly obtained. Then a solution of 4-methoxyl-benzenesulfonyl chloride (541 mg, 2.62 mmol) in acetonitrile (10 ml) was added dropwise and the mixture became slightly yellow coloured and was stirred at ambient temperature. TLC (EtOAc/Hexane, 1:1) monitoring showed the reaction was completed after 3 hours. After evaporation of acetonitrile, the residue was taken up in dichloromethane (30 ml) and extracted once each with 10% sodium bicarbonate solution (30 ml) and water (30 ml). Then the phases were separated and the dichloromethane phase was dried (Na2SO4), filtered and evaporated to afford the crude product. Flash chromatography using (Ethyl acetate/Hexane, 1:1) gave the pure product as a white solid. Yield 801 mg (93.90%).

8(b) 4-{[(1-tert-butoxycarbonyl-2-methyl-propyl)-(4-methoxy-benzenesulfonyl)-amino]-methyl}benzoic acid methyl ester (Compound 7*)

To a stirring solution of 2-(4-Methoxy-benzenesulfonylamino)-3-methyl-butyric acid tert-butyl ester (140 mg, 0.41 mmol) in acetonitrile (5 ml) at ambient temperature was added cesium carbonate (1.33 g, 4.10 mmol). Then methyl 4-(bromomethyl)benzoate (115 mg, 0.60 mmol) was added to the suspension and the reaction mixture was stirred at 70° C. for 1 hour by which time TLC (EtOAc/Hexane 1:1) monitoring showed the reaction to be completed. After cooling to ambient temperature, the mixture was filtered to remove excess cesium carbonate and evaporated to dryness. The residue was purified by flash chromatography (EtOAc/Hexane 1:1) to furnish the pure product as slightly yellow oil. Yield 153 mg (76%).

8(c) 4-{[(1-tert-butoxycarbonyl-2-methyl-propyl)-(4-methoxy-benzenesulfonyl)-amino]-methyl}-benzoic acid (Compound 8*)

The diester (Compound 7*) (151 mg, 0.31 mmol) was dissolved in tetrahydrofuran (2 ml) and 4N LiOH (250 µl) was added at ambient temperature. The mixture was heated to 60° C. for 5 hours when HPLC monitoring showed the hydrolysis was completed. The mixture was cooled to ambient temperature and the solvent was evaporated. The residue was dissolved in water and the clear solution extracted with once with diethyl ether. Then the aqueous phase was cooled to 5° C. (ice/water) and neutralised with 1N HCl and after which it was extracted with ethyl acetate (3×5 ml). The combined ethyl acetate phases was extracted with water (5 ml) and brine (5 ml), dried with ($Na_2SO4$), filtered and evaporated to afford the product as white foam. Yield 133 mg (90%).

8(d) 2-[(4-{5-(2-hydroxyimino-1,1-dimethyl-propylamino)-3-[2-(2-hydroxyimino-1,1-dimethyl propylamino)-ethyl]-pentylcarbamoyl}-benzyl)-(4-methoxy-benzenesulfonyl)-amino]-3-methyl-butyric acid tert-butyl ester (Compound 9*)

To the acid (Compound 8*) (61 mg, 0.13 mmol) in dimethylformamide (4 ml) was added N,N-diisopropyl ethylamine (46 µl, 0.26 mmol), N-[(dimethylamino)-1H-1,2,3-triazolo[4,5-b]pridin-1-ylmethylene]-N-methylmethanaminium hexafluorophosphate N-oxide, HATU (49 mg, 0.15 mmol) and C-Pn216 (51 mg, 0.15 mmol). The reaction mixture was stirred at ambient temperature and after 1 hour HPLC showed complete conversion to a new product. The mixture was evaporated to dryness and then pure product was isolated after flash chromatography (chloroform:methanol, 8/2) as white crystals. Yield 66 mg 8(e) 2-[(4-{5-(2-hydroxyimino-1,1-dimethyl-propylamino)-3-[2-(2-hydroxyimino-1,1-dimethyl-propylamino)-ethyl]-pentylcarbamoyl}-benzyl)-(4-methoxy-benzenesulfonyl)-amino]-3-methyl-butyric acid (Compound 10*)

Dichloromethane (4 ml) was added to the tert-butyl ester (Compound 9*) (64 mg, 0.08 mmol) and to the milky coloured solution which was obtained at ambient temperature was bobbled hydrochloric acid gas for 10 minutes. The mixture was evaporated to dryness and the residue was co-evaporated with dichloromethane (5×5 ml) to afford the product as off-white solid. Yield 58 mg (97%). M+1=747.

8(f) 4-{[(1-hydroxycarbamoyl-2-methyl-propyl)-(4-methoxy-benzenesulfonyl)-amino]methyl}-N-{5-(2-hydroxyimino-1,1-dimethyl-propylamino)-3-[2-(2-hydroxyimino-1,1-dimethyl-propylamino)-ethyl]-pentyl}-benzamide (Compound 11)

The hydroxamic acid was attached via tert-butyldimethylsilyl protected intermediate (Compound 11*). Thus, a mixture of the acid (Compound 10*) (57 mg, 0.76 mmol), 4-methylmorpholine (34 µl, 0.30 mmol), [7-azabenzotriazol-1-yloxytris(pyrrolidino)phosphonium-hexafluorophosphate] PyAOP, 40 mg, 0.076 mmol) and O-(tert-butyldimethylsilyl) hydroxylamine (12 mg, 0.08 mmol) in dimethylformamide (4 ml) was stirred at ambient temperature and the reaction monitored by HPLC. The reaction was stopped after 3 hours and solvents were evaporated. The residue was re-dissolved in dichloromethane and at ambient temperature, hydrochloric acid gas was bubbled through the mixture for 10 minutes. The mixture was evaporated to dryness and the residue co-evaporated with dichloromethane (5×5 ml). The product was obtained as a white powder after HPLC, M+H, 762. Yield 15 mg.

Example 9

Preparation of Compound 18

9(a) 2-[[4-(2-{2-[2-(2-azido-ethoxy)-ethoxy]-ethoxy}-ethylcarbamoyl)-benzyl]-(4-methoxy-benzenesulfonyl)-amino]-3-methyl-butyric acid tert-butyl ester (Compound 12*)

To the acid (Compound 8*; 140 mg, 0.30 mmol) in dimethylformamide (6 ml) was added N,N'-diisopropyl ethylamine (104.51 µl, 0.60 mmol), N-[(dimethylamino)-1H-1,2,3-triazolo[4,5-b]pridin-1-ylmethylene]-N-methylmethanaminium hexafluorophosphate N-oxide, HATU (114 mg, 0.30 mmol) and 2-{2-[2-(2-Azido-ethoxy)-ethoxy]-ethoxy}-ethylamine (65.50 mg, 0.30 mmol). The reaction mixture was stirred at ambient temperature and after 2 hours monitoring by HPLC showed complete conversion to a new product. The mixture was evaporated to dryness and then pure product was isolated after flash chromatography (ethyl acetate) as colourless oil. Yield 142 mg (70%).

9(b) 2-[[4-(2-{2-[2-(2-amino-ethoxy)-ethoxy]-ethoxy}-ethylcarbamoyl)-benzyl]-(4-methoxy-benzenesulfonyl)-amino]-3-methyl-butyric acid tert-butyl ester (Compound 13*)

To the stirring solution of the azide (Compound 12*; 200 mg, 0.29 mmol) in THF (5 ml) which was cooled to 0° C. (ice/$H_2O$) was added triphenylphosphine (84 mg, 0.32 mmol). After stirring at this temperature for 5 minutes the cooling bath was removed and stirring was continued at ambient temperature for 19 hours.

Then water (200 µl) was added and analysis (HPLC) after 15 hours indicated that hydrolysis was completed. The solvents were evaporated and oily residue purified by flash chromatography using firstly $CHCl_3$/Methanol (8:2) and then $CHCl_3$/MeOH/$H_2O$ to afford the compound as colourless oil. Yield 134 mg (71%). $M^+$ 652

9(c) 2-[{4-[2-(2-[2-[2-(4-carboxy-butyrylamino)-ethoxy]-ethoxy}-ethoxy)-ethylcarbamoyl]-benzyl]-(4-methoxy-benzenesulfonyl)-amino]-3-methyl-butyric acid tert-butyl ester CA1 (Compound 14*)

A solution of the amine (Compound 13*; 73 mg, 0.11 mmol), N,N-diisopropyl ethylamine (39 µl, 0.22 mmol), and the active ester 4-{5-(2-Hydroxyimino-1,1-dimethyl-propylamino)-3-[2-(2-hydroxyimino-1,1-dimethyl-propylamino)-ethyl]-pentylcarbamoyl}-thiobutyric acid 2,3,5,6-tetrafluoro-phenyl ester (b; 85 mg, 0.11 mmol) in dimethylformamide (5 ml) was stirred at ambient temperature for 2 hours when monitoring by HPLC showed the reaction had gone to completion. The mixture was evaporated to dryness and the residue purified by flash chromatography (CHCl/MeOH, 8:2) to afford the product as a gum. Yield 54 mg (45%).

9(d) 2-[{4-[2-(2-{2-[2-(4-carboxy-butyrylamino)-ethoxy]-ethoxy}-ethoxy)-ethylcarbamoyl]-benzyl}-(4-methoxy-benzenesulfonyl)-amino]-3-methyl-butyric acid cPn216. (Compound 15*)

Dichloromethane (5 ml) was added to the tert-butyl ester (Compound 14*; 50 mg, 0.046 mmol) and to the milky coloured solution which was obtained at ambient temperature was bobbled hydrochloric acid gas for 10 minutes. The mixture was evaporated to dryness and the residue was co-evaporated with dichloromethane (5×5 ml) to afford the product as white solid. Yield 47 mg (99%). M+1=1035.

9(e) 4-[2-(2-{2-[2-(4-{[(1-hydroxycarbamoyl-2-methyl-propyl)-(4-methoxy-benzenesulfonyl)-amino]-methyl}-benzoylamino)-ethoxy]-ethoxy}-ethoxy)-ethylcarbamoyl]-butyric acid cPn216 (Compound 18)

The hydroxamic acid function was attached via tert-butyldimethylsilyl protected intermediate. Thus, a mixture of the acid (Compound 15*; 47 mg, 0.045 mmol), 4-methylmorpholine (20 μl, 0.18 mmol), [7-azabenzotriazol-1-yloxytris(pyrrolidino)phosphonium-hexafluorophosphate] PyAOP (a; 23.5 mg, 0.045 mmol) and O-(tert-butyldimethylsilyl)hydroxylamine (10 mg, 0.07 mmol) in dimethylformamide (3 ml) was stirred at ambient temperature and the reaction monitored by HPLC. The reaction was stopped after 1 hour and solvents were evaporated. The residue was re-dissolved in dichloromethane and at ambient temperature, hydrochloric acid gas was bobbled through the mixture for 10 minutes. The mixture was evaporated to dryness and the residue co-evaporated with dichloromethane (5×5 ml). The product was obtained as a white powder after HPLC, M+H, 1050, Yield 7 mg (15%)

Example 10

Preparation of Compound 19

10(a) 2-[{4-[2-(2-{2-[2-(2-carboxymethoxy-acetylamino)-ethoxy]-ethoxy}-ethoxy)-ethylcarbamoyl]-benzyl}-(4-methoxy-benzenesulfonyl)-amino]-3-methyl-butyric acid tert-butyl ester (Compound 17*)

A mixture of the amine (Compound 13*; 60 mg, 0.092 mmol), N,N'-diisopropyl ethylamine (96 μl, 0.55 mmol), and diglycolic anhydride (66 mg, 0.55 mmol) in dimethylformamide (6 ml) was stirred at ambient temperature for 3 hours when monitoring by HPLC indicated complete reaction. The solvent was removed under reduced pressure and the residue dissolved in acetonitrile containing 0.1% TFA. After stirring for 5 minutes, the mixture was evaporated to dryness and the crude product purified by flash chromatography using $CHCl_3MeOH/H_2O$, 65:25:4. The product was obtained as white foam. Yield 70.50 mg (99.80%).

10(b) 2-[{4-[2-(2-{2-[2-(2-carboxymethoxy-acetylamino)-ethoxy]-ethoxy}-ethoxy)-ethylcarbamoyl]-benzyl}-(4-methoxy-benzenesulfonyl)-amino]-3-methyl-butyric acid tert-butyl ester-CA1 conjugate (Compound 18*)

To the acid (Compound 17*; 70.50 mg, 0.092 mmol) in dimethylformamide (5 ml) was added N,N-diisopropyl ethylamine (32 μl, 0.184 mmol), N-[(dimethylamino)-1H-1,2,3-triazolo[4,5-b]pridin-1-ylmethylene]-N-methylmethanaminium hexafluorophosphate N-oxide, HATU (38 mg, 0.10 mmol) and chelating agent 1 (CA1; 34 mg, 0.10 mmol). The reaction mixture was stirred at ambient temperature and after 6 hour HPLC showed substantial conversion to a new product. The mixture was evaporated to dryness and then pure product was isolated after preparatory HPLC chromatography acetonitrile:water:0.1% trifluoroacetic acid (10:80:60) as white crystals. Yield 21 mg (21%).

10(c) 2-[{4-[2-(2-{2-[2-(2-carboxymethoxy-acetylamino)-ethoxy]-ethoxy}-ethoxy)-ethylcarbamoyl]-benzyl}-(4-methoxy-benzenesulfonyl)-amino]-3-methyl-butyric acid-CA1 conjugate (Compound 19*)

Dichloromethane (3 ml) was added to the tert-butyl ester (Compound 18*; 20 mg, 0.018 mmol) and to the milky coloured solution which was obtained at ambient temperature was bobbled hydrochloric acid gas for 60 minutes. The mixture was evaporated to dryness and the residue was co-evaporated with dichloromethane (5×5 ml) to afford the product as off-white solid. Yield 18 mg (95%). M+1=1037.

10(d) {[2-[2-{2-[2-(4-{[(1-hydroxycarbamoyl-2-methyl-propyl)-(4methoxy-benzenesulfonyl)-amino]-methyl]-benzoylamino)-ethoxy]-ethoxy}-ethoxy)-ethylcarbamoyl]-methoxy}-acetic acid-CA1 conjugate (Compound 19)

The hydroxamic acid was attached via tert-butyldimethylsilyl protected intermediate. Thus, a mixture of the acid (Compound 19*; 18 mg, 0.017 mmol), 4-methylmorpholine (8 μl, 0.70 mmol), [7-azabenzotriazol-1-yloxytris(pyrrolidino)phosphonium-hexafluorophosphate] PyAOP(9.4 mg, 0.017 mmol) and O-(tert-butyldimethylsilyl)hydroxylamine (4 mg, 0.026 mmol) in dimethylformamide (2 ml) was stirred at ambient temperature and the reaction monitored by HPLC. The reaction was stopped after 2 hours and solvents were evaporated. The residue (Compound 20*) was re-dissolved in dichloromethane and at ambient temperature; hydrochloric acid gas was bubbled through the mixture for 10 minutes. The mixture was evaporated to dryness and the residue co-evaporated with dichloromethane (5×3 ml). The product was obtained as a white powder after HPLC, M+H, 1052. Yield 4 mg (22.35%).

Example 11

$^{99m}$Tc Labelling of Compounds 10, 11, 12, 18 and 19 to Produce Compounds 1, 2, 3, 16 and 17, Respectively A $SnCl_2$/MDP solution is prepared by dissolving 10 mg $SnCl_2$ and 90 mg MDP in 100 ml of nitrogen-purged saline. To 50 μl 1 mg/ml in methanol of one of Compounds 10, 11 or 12, is added; (1) 0.7 ml methanol, (2) 0.5 ml 0.1M sodium carbonate buffer, (3) 0.5 ml 500 MBq/ml $TcO_4$, and (4) 100 μl of the $SnCl_2$/MDP solution. This reaction mixture is heated at 37° C. for 30 min to form one of Compounds 1, 2 or 3, respectively.

Example 12

Preparation of Compound 4

Figure 6:
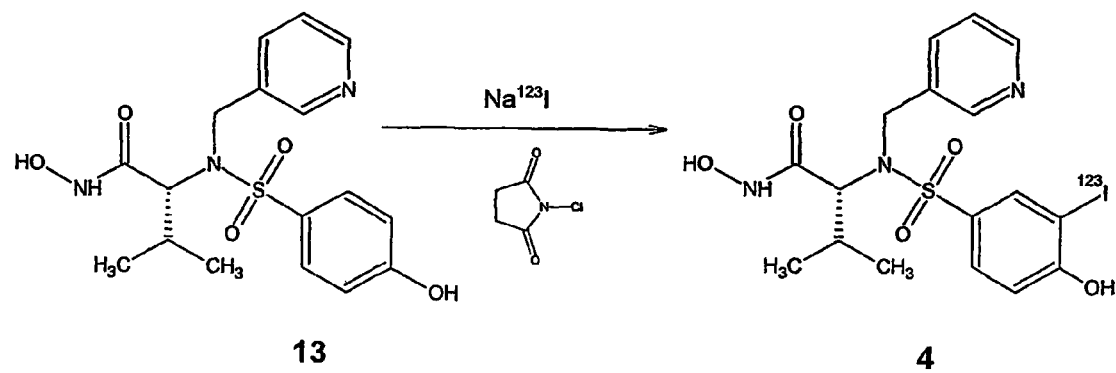
FIG. 6 illustrates the radiosynthesis of Compound 4 via radioiodination of Compound 13.

FIG. 6 illustrates the synthetic route for the preparation of Compound 4. 4 μl [$^{123}$I]NaI in 0.05 N NaOH solution (12.04

MBq), 39 µl Compound 13 solution (c=1.23 g/l MeOH) and 71 µl NCS-solution (NCS=N-chlorosuccinimide) (c=0.579 g/l water for injection) were added to a conical vial.

The mixture was vortexed for 1 min and then shaken for 60 min at room temperature in the dark. Then 25 µl $Na_2S_2O_3$-solution (c=2.00 g/l water for injection) was added and the mixture was vortexed again.

The solution was injected to the gradient HPLC-chromatograph with γ- and UV-detector and a Nucleosil™ reverse-phase C-18 5µ 250×4 $mm^2$ column with a corresponding 20×4 $mm^2$ precolumn.

| HPLC-conditions: | eluent A: | $CH_3CN/H_2O$/TFA 950/50/1 |
| --- | --- | --- |
| | eluent B: | $CH_3CN/H_2O$/TFA 50/950/1 |
| | time-program: | eluent B from 92% to 50% within 45 min and then from 50% to 92% within 10 min |
| | Flow: | 1.5 ml/min |
| | λ: | 254 nm |
| | $R_t$(product-fraction): | 18.50–19.80 min |

This fraction was evaporated to dryness, redissolved in 200 µl PBS-buffer and reinjected to the gradient HPLC using the same conditions (see above).

$R_t$(Compound 4): 17.40-18.70 min

The quality-control of this product (HPLC, same conditions) didn't show any impurities in the γ- and UV-chanel. The radiochemical yield was 44%.

Example 13

Preparation of Compound 5

Compound 5 is the $^{125}$I version of Compound 4. It was prepared using the method described in Example 12 apart from the use of [$^{125}$I]NaI instead of [$^{123}$I]NaI.

Example 14

Preparation of Compound 6

0.6 mg 2,5-dihydroxybenzoic acid, 0.8 mg ascorbic acid, 20 µl water for injection and 5 µl $CuSO_4$.5 $H_2O$ solution (c=3.26 g/l water for injection) was added to a conical vial containing 50 µl Compound 14 (c=2.00 g/l EtOH). The ice-cooled mixture was degassed for 10 min using a He-flow. Then 4 µl [$^{125}$I]NaI in 0.05 N NaOH solution (8.68 MBq) was added and vortexed. The mixture was heated up to 113° C. for 51 min and shaken every 5 min. After cooling to RT the mixture was diluted with 40 µl EtOH. The solution was then injected to the HPLC-chromatograph and HPLC was carried out as described in Example 10. $R_t$ (product fraction): 17.18-19.54 min.

The fraction was evaporated to dryness, redissolved in 200 µl $CH_3CN/H_2O$/TFA: 50/950/1, and reinjected to the gradient HPLC. $R_t$ Compound 6: 21.05-21.36 min.

In the quality control of the product by HPLC no impurities could be detected within the γ- and UV-channel. The $R_t$ parameters were realized by adding an aliquot of Compound 9 (i.e. non-radioactive Compound 6) to a second quality control injection.

Average radiochemical yield: 23% (n=5).

Example 15

Preparation of Compound 7

Compound 7 is prepared via the same route as Compound 6 except that [$^{123}$I]NaI is used instead of [$^{125}$I]NaI.

Example 16

Preparation of Compound 15

Figure 7:
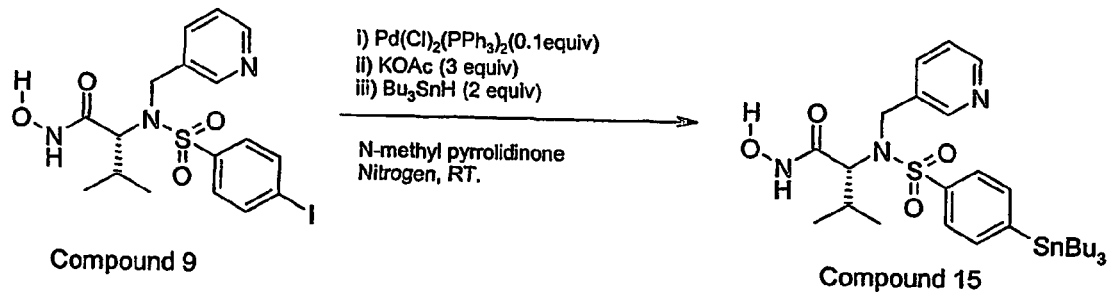
FIG. 7 illustrates two alternative synthetic routes used for the preparation of the precursor Compound 15.
Figure 7:
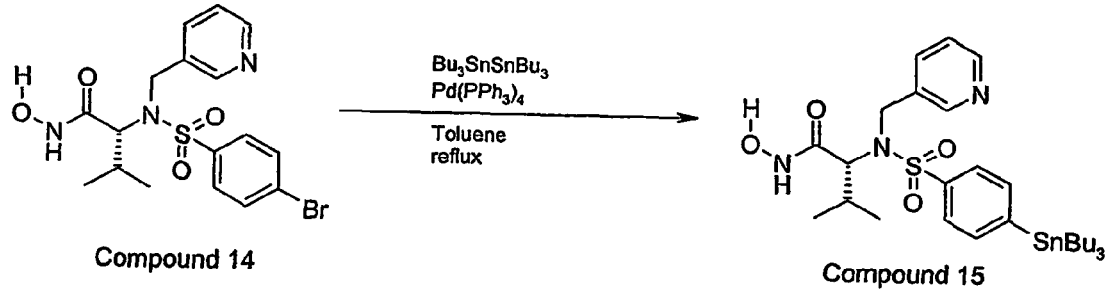

The synthetic routes that can be used in the preparation of Compound 15 are illustrated in FIG. 7.

In Synthetic Route A, a flask is charged with nitrogen followed by sequential addition of dichloro(bistriphenylphosphine) palladium(II) (0.1 equiv) and potassium acetate(3 equiv). N-methyl pyrrolidinone (5 ml) is added followed sequentially by Compound 9 (1 equiv) and tributyltin hydride (2 equiv). The reaction mixture is stirred for 24 hours at room temperature. The reaction mixture is then diluted with ethyl acetate, washed with water, and dried over magnesium sulphate. The solvent is evaporated and the product is isolated after HPLC purification.

In Synthetic Route B, a flask is charged with nitrogen followed by the addition of Compound 14 and anhydrous toluene. To this is added sequentially hexabutylditin and tetrakistriphenylphosphine palladium. The reaction mixture is heated at reflux for 24 hours to obtain the product.

Example 17

Preparation of Compound 7

10 µl of 0.1 mM $Na^{127}$I in 0.01 M NaOH was added to 200 µl 0.2 M $NH_4OAc$ (pH 4). The $Na^{127}I/NH_4OAc$ solution was then added to 11.0 µl $Na^{123}$I in 0.05 M NaOH (111 MBq). The combined solution was transferred to a silanised plastic vial. A solution of peracetic acid was prepared by adding 5 µl of 36-40 wt % peracetic acid solution in acetic acid to 5 ml $H_2O$. 5 µl of the prepared peracetic acid solution was then added to the vial containing the $Na^{123}I^{127}$I. Finally, 17 µl of a 3 mM solution of the tributyl tin precursor (Compound 15) in a silanised plastic vial was added to the reaction mixture and the solution was allowed to stand for 3 min.

Compound 7 can be analysed or purified using gradient HPLC chromatography with γ- and UV-detectors and a reverse-phase Phenomenex $C_{18}$(2) Luna 5µ, 150×4.6 mm column.

HPLC-conditions eluant A: 0.1% TFA in $H_2O$
eluant B: 0.1% TFA in $CH_3CN$
eluant B from 20% to 80% over 20 min.
20 min 80% B
20.2 min 100% B
23.2 min 100% B
23.7 min 20% B
Flow: 1 ml/min
λ: 254 nm
$R_T$: 7 min Example 18

Assay for MMP-2 and MMP-9 Inhibitory Activity

The synthetic broad-spectrum fluorogenic substrate (7-methoxycoumarin-4-yl) acetyl pro-Leu-Gly-Leu-(3-(2,4-dinitrophenyl)-L-2,3-diamino-propionyl)-Ala-Arg-$NH_2$ (R & D Systems) was used to assay MMP-2 and MMP-9 activity as described previously [Huang et al J. Biol. Chem. 272 22086-22091 (1997)]. The inhibition of MMP-2 and MMP-9 by CGS 27023 and Compounds 8, 9, 13 and 14, was assayed by preincubating either MMP-2 (1 nM) or MMP-9 (2 nM), and the compounds to be assayed at varying concentrations (10 pm-1 mM) in 50 mM Tris-HCl, pH 7.5, containing 0.2 M NaCl, 5 mM $CaCl_2$, 20 µM $ZnSO_4$ and 0.05% Brij 35 at 37° C. for 30 min. An aliquot (10 µl) of substrate (5 µM) was then added to 90 µM of preincubated MMP/compound mixture, and activity was determined at 37° C. by following product release with time. The fluorescence changes were monitored using a Fusion Universal Microplate Analyzer (Packard Bioscience) with excitation and emission wavelengths set to 330 and 390 nm, respectively for MMP-2 and MMP-9. Inhibited rates were measured from the initial 10 min of the reaction profile where product release was linear with time. Nonlinear regression analysis was performed using the XMGRACE 5.18 software under linux.

Table 2 below gives the $IC_{50}$ values obtained for the compounds assayed.

TABLE 2

Inhibition effects of Compounds 8, 9, 13 and 14 on MMP-2 and MMP-9 activity compared to CGS 27023A.

| Compound | MMP-2 [nM] | MMP-9 [nM] |
|---|---|---|
| Compound 8 | 320 | 153 |
| Compound 9 | 2.5 | 4.6 |
| Compound 13 | 57.5 | 257 |
| Compound 14 | 16.2 | 76.0 |
| CGS 27023A | 11.2 | 59.6 |

Example 19

ApoE (−/−) Mouse Model $ApoE^{-/-}$ mice (4 weeks old, 20 to 28 g) were anesthetized by intraperitoneal injection of xylazine/ketamine (Bayer, Germany). The left common carotid artery was ligated near the bifurcation using 5-0 silk (Ethicon). In sham-operated controls, the suture was passed under the left common carotid artery without tightening. The animals were allowed to recover for one week and then put on a high cholesterol diet (15% cocofat, 1.0% cholesterol, 0.5% sodium-cholate). Five weelks after surgery mice were used for histopathological, autoradiographical and imaging studies.

Example 20

Histology and Immunohistochemistry

ApoE −/− mice, as described in Example 16, were perfused with Langendorff buffer for 3 minutes. The ligation sites and left and right carotid arteries were removed and snap-frozen in liquid nitrogen without further dissection. Groups of 5 sections (10 µm for histopathology) were collected at equally spaced intervals.

Serial cryostat sections (10 µm) of surgical specimens of the ligation sites and the left and right common carotid arteries were cut, air dried onto microscope slides, fixed in 10 min 3.75% PFA (MMP-9), 4° C. acetone 10 min (MAC3, 550292, BD Pharmingen, California, USA). Sections were stained with hematoxylin and eosin. For immunohistochemistry, 10 min, anti-peroxidase reagent (S2001, DAKO, Denmark), 1% BSA 25 min, sections were incubated (30 minutes) with primary (2 µg/ml rabbit anti-mouse MMP-9, AB19047, Chemicon, Germany) or control (rabbit IgG, E0432, DAKO, Denmark) antibody 1 h RT in antibody diluent with background reducing components (S3022, DAKO, California, USA) and processed according to the suppliers' recommendations. Goat anti-rabbit IgG (H+L) biotin conjugated (AB132B, 1:500, Chemicon, Germany) 25 min. Streptavidin-HRP (LSAB kit, K0675, California, USA) 25 min, AEC (K0696, DAKO, California, USA) 20 min, hematoxylin 1 min, $H_2O$ 1-2 min.

Figure 8:
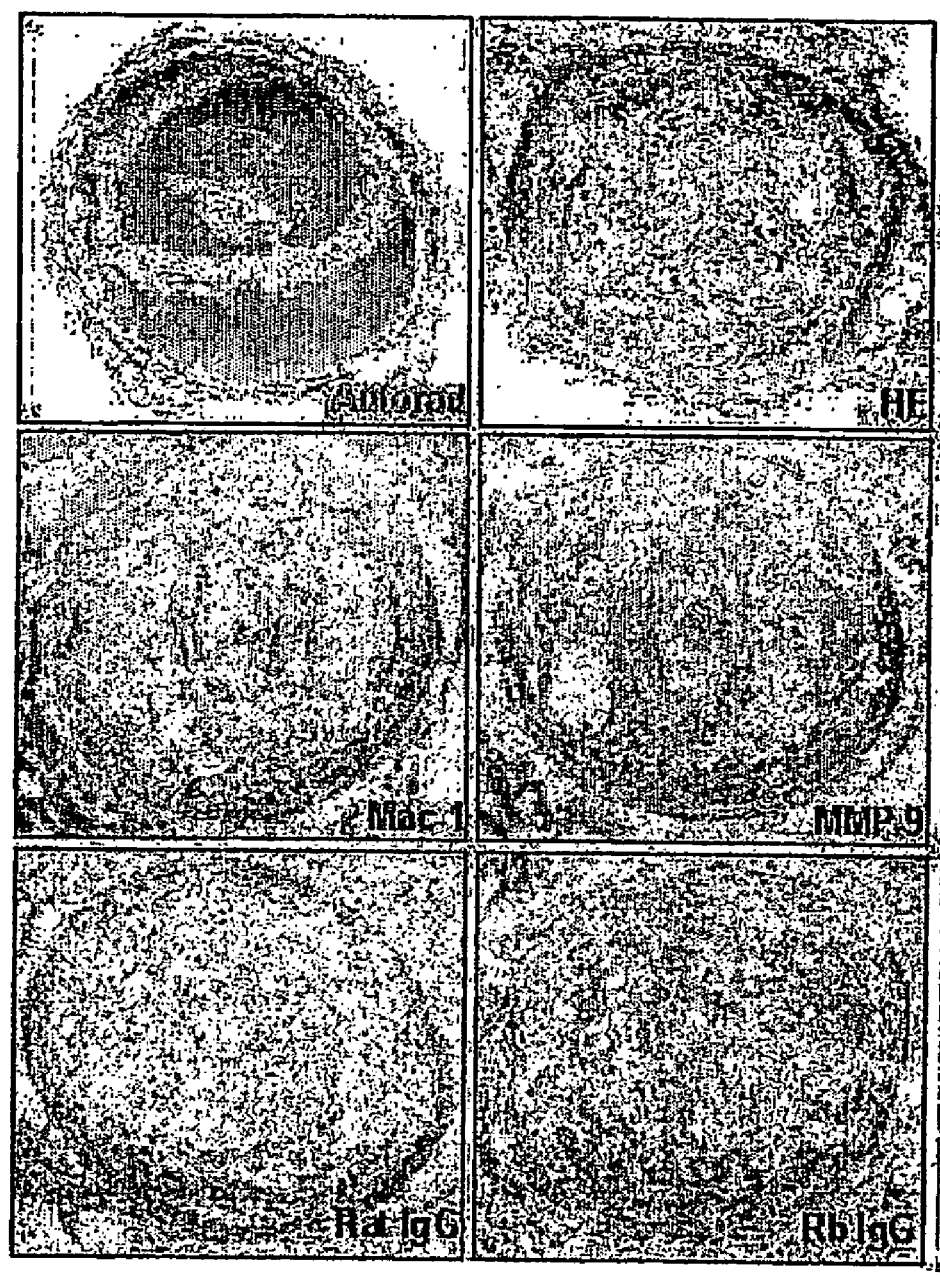
FIG. 8 illustrates the results of the immunohistochemistry carried out on samples of left carotid artery taken from the ApoE(−/−) mice. HE=hematoxylin and eosin.

FIG. 8 illustrates the immunohistochemistry results as well as the autoradiography results, which show that uptake correlated with the presence of MMP-9.

Example 21

In vivo Autoradiography

Four ligated ApoE−/− mice were injected retroorbitally with 0.5 µCl (20 MBq) of Compound 5 in 0.2 ml 0.9% NaCl and CGS 27023 (6 mM in 200 µl of 0.9% NaCl for nonspecific binding) or saline 2 h prior to the radioligand, mice were sacrificed 2 hours p.i. The ligation site and the left and right common carotid arteries were quickly removed, cut into frozen sections, then 60-µm thick sections were processed for microautoradiography.

FIG. 8 illustrates the autoradiography results in conjuction with the immunohistochemistry results as discussed in Example 17.

Example 22

In Vivo Imaging

Compound 4 was injected via the retroorbital venous plexus and planar imaging was carried out on a Siemens MULTISPECT 3 gamma camera with a ultrahigh resolution collimator. Dynamic images were acquired with an original framing of 1 min frames which was summed to 10 min frames for analysis. Plaque area was analysed by circular ROIs (region of interest) and TACs (time activity curves) were created.

Figure 9:
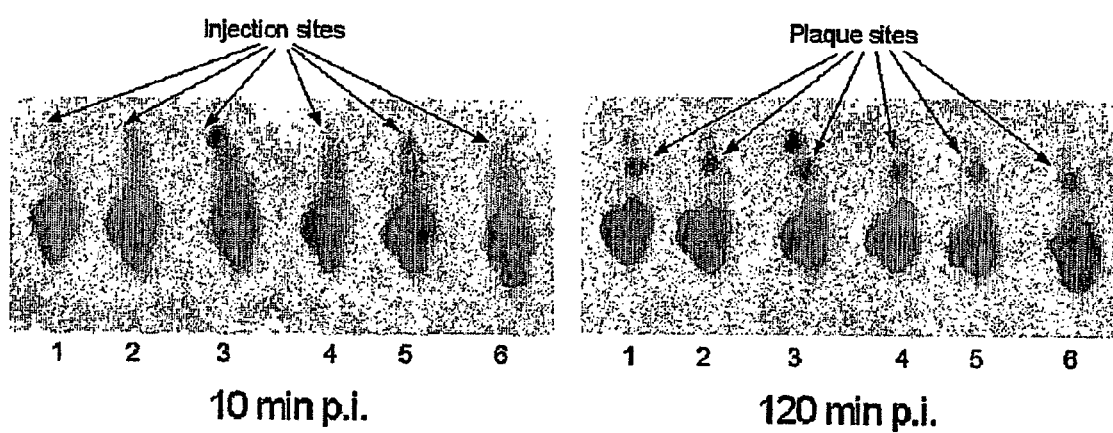
FIG. 9 illustrates the images produced in ApoE(−/−) mice after injection of Compound 4.

Experiment A: 9 MBq of Compound 4 in 200 µl of 0.9% NaCl was injected into each mouse (mice 1 to 6) and dynamic images taken up to 120 min post injection. TACs were created and showed increasing uptake of the labelled compound in the area of ligation over 120 min (see FIG. 9).

Figure 10:
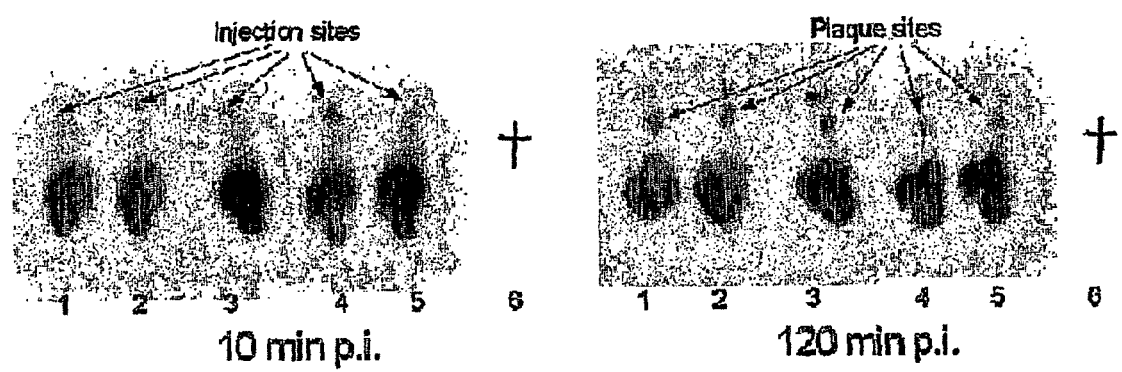
FIG. 10 illustrates a comparison of the uptake of Compound 4 in ApoE(−/−) mice without pre-dosing of cold compound and in ApoE(−/−) mice after pre-dosing with the cold compound, CGS27023.
Figure 11:
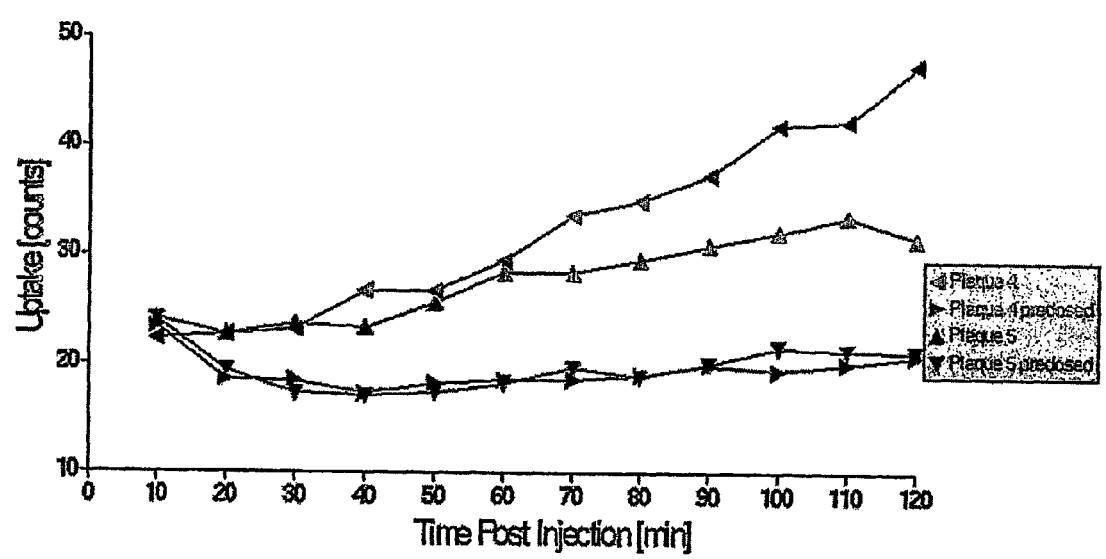
FIG. 11 shows the time-activity curves produced uptake in mice 4 and 5 without pre-dosing in Experiment A and after pre-dosing in Experiment B showed lower uptake in pre-dosed animals.

Experiment B: 2 days later 6 mM of CGS 27023 in 200 µl 0.9% NaCl was injected into mice 4 and 5 from the previous experiment 2 hours prior injection of 7.5 MBq of Compound 4 in 200 µl 0.9% NaCl. Mice 1 to 3 were also injected with 7.5 MBq of Compound 4 in 200 µl 0.9% NaCl without cold pre-dosing. Dynamic images were acquired over 120 minutes (FIG. 10) and TACs created. Comparison of the uptake in mice 4 and 5 without pre-dosing in Experiment A and after pre-dosing in Experiment B showed lower uptake in pre-dosed animals (see FIG. 11).

Additional ROIs were drawn over the liver, kidneys, bladder, brain and the thorax during Experiment A. for each ROI decay-corrected TACs were calculated and normalised to the 10 min p.i. activity, i.e. normalised counts per second (see FIG. 12).

The invention claimed is:

1. A diagnostic imaging agent:

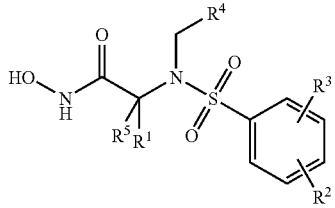

(I)

wherein:
- $R^1$ is selected from hydrogen, hydroxy, $C_{1-6}$ alkyl, $C_{6-14}$ aryl, $C_{7-20}$ arylalkyl, or together with $R^5$ and the carbon to which it is attached forms either a $C_{6-8}$ cycloalkyl ring or a $C_{4-6}$ heterocyclic ring, or together with $R^4$ forms a $C_{4-6}$ heterocyclic ring containing 5-7 atoms and 1 or 2 heteroatoms chosen from N or O;
- $R^2$ is a γ-emitting isotope of iodine attached via a direct covalent bond to the 3- or 4-position of the aromatic ring;
- $R^3$ is hydrogen;
- $R^4$ is $C_{6-14}$ aryl, $C_{4-6}$ heteroaryl, $C_{7-20}$ arylalkyl, $C_{7-20}$ carbamoylaryl or arylcarbamoylaryl; and,
- $R^5$ is selected from hydrogen or $C_{1-6}$ alkyl.

2. The diagnostic imaging agent of claim 1 wherein:
- $R^1$ is selected from $C_{1-6}$ alkyl, $C_{6-14}$ aryl, or $C_{7-20}$ arylalkyl, or together with $R^5$ forms a $C_{4-6}$ heterocyclic ring together with the carbon to which it is attached;
- $R^4$ is pyridyl or $(Ar^1)_y$-$(R''')_z$(NH)-phenyl wherein $Ar^1$ is phenylene, $R'''$ is $CH_2$ or $C=O$, $y=0$ or 1 and $z=0$ or 1; and,
- $R^5$ is hydrogen.

3. The diagnostic imaging agent of claim 1 wherein:
- $R^1$ is methyl, isobutyl, isopropyl, benzyl or hydroxybenzyl;
- $R^4$ is pyridyl or $(Ar^1)_y$-$(R''')_z$(NH)-phenyl wherein $Ar^1$ is 1,4-phenylene, $R'''$ is $CH_2$ or $C=O$, $y=0$ or 1 and $z=0$ or 1; and
- $R^5$ is hydrogen.

4. The diagnostic imaging agent of claim 1 wherein $R^5$ is hydrogen and the diagnostic imaging agent is of Formula Ia:

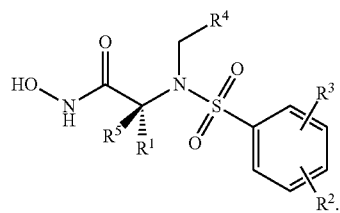

(Ia)

5. The diagnostic imaging agent of claim 1 wherein $R^2$ is positioned para to the sulfonamide.

6. The diagnostic imaging agent of claim 1, wherein said γ-emitting isotope of iodine is $^{123}$I.

7. A pharmaceutical composition comprising the diagnostic imaging agent of claim 1 together with a biocompatible carrier, in a form suitable for mammalian administration.

8. A kit for the preparation of a pharmaceutical composition comprising a precursor useful in the preparation of the diagnostic imaging agent of claim 1, wherein said precursor is a compound of Formula I

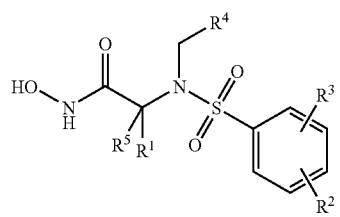

(I)

wherein:
- $R^1$ is selected from hydrogen, hydroxy, $C_{1-6}$ alkyl, $C_{6-14}$ aryl, $C_{7-20}$ arylalkyl, or together with $R^5$ and the carbon to which it is attached forms either a $C_{6-8}$ cycloalkyl ring or a $C_{4-6}$ heterocyclic ring, or together with $R^4$ forms a $C_{4-6}$ heterocyclic ring containing 5-7 atoms and 1 or 2 heteroatoms chosen from N or O;
- $R^2$ is hydroxy, tributyltin, or $^{127}$I;
- $R^3$ is hydrogen;
- $R^4$ is $C_{6-14}$ aryl, $C_{4-6}$ heteroaryl, $C_{7-20}$ arylalkyl, $C_{7-20}$ carbamoylaryl or arylcarbamoylaryl; and,
- $R^5$ is selected from hydrogen or $C_{1-6}$ alkyl.

* * * * *